(12) United States Patent
Nomoto et al.

(10) Patent No.: US 10,092,463 B2
(45) Date of Patent: Oct. 9, 2018

(54) NONWOVEN AND ABSORBENT ARTICLE HAVING A BLOOD SLIPPING AGENT

(71) Applicant: UNICHARM CORPORATION, Shikokuchuo-shi, Ehime (JP)

(72) Inventors: Takashi Nomoto, Kanonji (JP); Yuichi Suzuki, Kanonji (JP); Takashi Onozuka, Kanonji (JP); Akira Hashino, Kanonji (JP); Yuki Noda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/431,951

(22) PCT Filed: Sep. 12, 2013

(86) PCT No.: PCT/JP2013/074735
§ 371 (c)(1),
(2) Date: Mar. 27, 2015

(87) PCT Pub. No.: WO2014/050600
PCT Pub. Date: Apr. 3, 2014

(65) Prior Publication Data
US 2015/0238375 A1 Aug. 27, 2015

(30) Foreign Application Priority Data
Sep. 30, 2012 (JP) .................................. 2012-218979

(51) Int. Cl.
*A61F 13/15* (2006.01)
*A61F 13/20* (2006.01)
(Continued)

(52) U.S. Cl.
CPC ........ *A61F 13/8405* (2013.01); *A61F 13/472* (2013.01); *A61F 13/5121* (2013.01);
(Continued)

(58) Field of Classification Search
CPC ............ A61F 13/53; A61F 2013/15308; A61F 2013/530218; A61F 2013/530233;
(Continued)

(56) References Cited

U.S. PATENT DOCUMENTS

| 2003/0082219 A1* | 5/2003 | Warren | A61F 13/512 |
| | | | 424/401 |
| 2005/0180942 A1* | 8/2005 | Shimizu | A61K 8/31 |
| | | | 424/70.31 |

(Continued)

FOREIGN PATENT DOCUMENTS

| AU | 2013227547 A1 | 9/2014 |
| EP | 2835117 A1 | 2/2015 |

(Continued)

OTHER PUBLICATIONS

International Search Report dated Nov. 12, 2013 in International Application No. PCT/JP2013/074735, 2 pages.

(Continued)

*Primary Examiner* — Michele M Kidwell
(74) *Attorney, Agent, or Firm* — Hauptman Ham, LLP

(57) ABSTRACT

The purpose of the present invention is to provide a nonwoven for a top sheet of an absorbent article that is unlikely to stick after having absorbed menstrual blood, that is smooth and dry, and in which the absorbed menstrual blood is unlikely to diffuse on the nonwoven. This nonwoven has the following configuration. A nonwoven for a top sheet of an absorbent article, having a lengthwise direction and a crosswise direction, wherein the nonwoven has a plurality of ridge parts and a plurality of groove parts extending in the lengthwise direction and disposed in alternating fashion in the crosswise direction, the nonwoven being characterized in that the ridge parts and the groove parts have a plurality of through-holes, and the ridge parts have a region contain- (Continued)

ing a blood lubricity-imparting agent that contains a predetermined blood lubricity-imparting agent.

18 Claims, 7 Drawing Sheets

(51) Int. Cl.
    *A61F 13/84* (2006.01)
    *A61F 13/472* (2006.01)
    *A61F 13/511* (2006.01)
    *A61L 15/20* (2006.01)
    *A61L 15/50* (2006.01)
    *D06M 13/10* (2006.01)
    *A61F 13/512* (2006.01)

(52) U.S. Cl.
    CPC .. *A61F 13/51104* (2013.01); *A61F 13/51108* (2013.01); *A61F 13/51113* (2013.01); *A61L 15/20* (2013.01); *A61L 15/50* (2013.01); *D06M 13/10* (2013.01); *A61F 2013/8455* (2013.01); *D06M 2200/00* (2013.01)

(58) Field of Classification Search
    CPC ........ A61F 2013/530299; A61F 2013/530343; A61F 2013/53043; A61F 2013/530615; A61F 2013/5395
    See application file for complete search history.

(56) References Cited

U.S. PATENT DOCUMENTS

| | | |
|---|---|---|
| 2007/0298213 A1 | 12/2007 | Noda et al. |
| 2007/0298214 A1 | 12/2007 | Noda et al. |
| 2007/0298220 A1 | 12/2007 | Noda et al. |
| 2007/0298667 A1 | 12/2007 | Noda et al. |
| 2007/0298671 A1 | 12/2007 | Noda et al. |
| 2007/0299416 A1 | 12/2007 | Noda et al. |
| 2008/0010795 A1 | 1/2008 | Mizutani et al. |
| 2008/0044622 A1 | 2/2008 | Noda et al. |
| 2008/0044628 A1 | 2/2008 | Noda et al. |
| 2008/0045915 A1 | 2/2008 | Noda et al. |
| 2008/0085399 A1 | 4/2008 | Noda et al. |
| 2008/0200894 A1 | 8/2008 | Gatto et al. |
| 2009/0221978 A1 | 9/2009 | Gatto et al. |
| 2009/0282660 A1 | 11/2009 | Noda et al. |
| 2010/0151054 A1* | 6/2010 | Nishioku ............... A61K 8/06 424/678 |
| 2012/0123365 A1* | 5/2012 | Pan ........................ A61K 8/0208 604/367 |
| 2012/0226250 A1* | 9/2012 | Sato ................... A61F 13/51104 604/367 |
| 2013/0197462 A1* | 8/2013 | Abuto .................... A61F 13/512 604/378 |
| 2014/0052086 A1 | 2/2014 | Komatsu et al. |
| 2014/0228793 A1* | 8/2014 | Hashino ................ A61F 13/511 604/367 |
| 2015/0018796 A1* | 1/2015 | Tamura ............. A61F 13/51104 604/385.04 |
| 2015/0028252 A1* | 1/2015 | Saito ...................... C09K 5/045 252/68 |
| 2015/0032074 A1 | 1/2015 | Nakashita et al. |
| 2015/0065978 A1* | 3/2015 | Uda ....................... A61F 13/534 604/370 |
| 2015/0223997 A1* | 8/2015 | Noda ...................... A61L 15/42 604/381 |

FOREIGN PATENT DOCUMENTS

| | | | |
|---|---|---|---|
| EP | 2901974 A1 | 8/2015 | |
| JP | 2002-238947 A | 8/2002 | |
| JP | 2008-002034 A | 1/2008 | |
| JP | 2008-025083 A | 2/2008 | |
| JP | 2010-518918 A | 6/2010 | |
| JP | 2011-510801 A | 4/2011 | |
| JP | 2012-236001 A | 12/2012 | |
| WO | 2008/101163 A2 | 8/2008 | |
| WO | 2009/102837 A2 | 8/2009 | |
| WO | 2011/065247 A1 * | 6/2011 | ............ A61F 13/49 |
| WO | 2013/129236 A1 | 9/2013 | |

OTHER PUBLICATIONS

Fujita, A., "Prediction of Organic Compounds and Organic Conceptual Diagram," Journal of Japanese Chemistry, vol. 11, No. 10, Oct. 1957, pp. 719-725.

\* cited by examiner (a)

(b)

NONWOVEN AND ABSORBENT ARTICLE HAVING A BLOOD SLIPPING AGENT

RELATED APPLICATIONS

The present application is a National Phase of International Application Number PCT/JP2013/074735 filed Sep. 12, 2013 and claims priority of Japanese Application Number 2012-218979 filed Sep. 30, 2012.

TECHNICAL FIELD

The present disclosure relates to a nonwoven fabric, and to an absorbent article comprising the nonwoven fabric as a top sheet.

BACKGROUND ART

As the basic performance of absorbent articles, such as sanitary napkins and panty liners has continued to improve with technological development over many years, leakage after absorption of excreta, such as menstrual blood has become a less frequent occurrence than in the past, and research is currently ongoing with the aim of achieving even higher performance, including a feel similar to underwear, and smoothness of the top sheet even after absorption of excreta, such as menstrual blood.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

Nonwoven fabrics for use in top sheets of absorbent articles in the relevant technical field include the one described in PTL 1, for example. The nonwoven fabric described in PTL 1 is designed to provide a nonwoven fabric that has been modified so as to be permeable to fluids at projections, recesses and the like.

Absorbent articles are also known in the technical field that are coated with lotion compositions.

For example, PTL 2 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet.

Also, PTL 3 discloses an absorbent article wherein a polypropylene glycol material-containing lotion composition is applied on the outer surface of the top sheet (body side surface).

CITATION LIST

Patent Literature

PTL 1 Japanese Unexamined Patent Publication No. 2008-25083
PTL 2 Japanese Unexamined Patent Publication No. 2010-518918
PTL 3 Japanese Unexamined Patent Publication No. 2011-510801

SUMMARY OF INVENTION

Technical Problem

The nonwoven fabric described in PTL 1 is designed to be permeable to fluids, but some of the fibers composing the projections are oriented in the longwise direction, often causing diffusion of the absorbed menstrual blood in the longwise direction at the projections. Further improvement in the function of fluid permeability has therefore been considered for the nonwoven fabric described in PTL 1.

It is therefore an object of the present disclosure to provide a nonwoven fabric for an absorbent article top sheet, that has low stickiness and is light after absorption of menstrual blood, and that has low diffusion of absorbed menstrual blood on the nonwoven fabric.

Solution to Problem

As a result of diligent research directed toward solving the problems described above, the present inventors have discovered a nonwoven fabric for a top sheet of an absorbent article, having a longwise direction and a crosswise direction, the nonwoven fabric having a plurality of ridges and a plurality of furrows extending in the longwise direction and alternately disposed in the crosswise direction, wherein the plurality of ridges and the plurality of furrows each have a plurality of through-holes, the ridges having blood lubricity imparter-containing regions that contain a blood slipping agent with a kinematic viscosity of 0.01 to 80 $mm^2/s$ at 40° C., a water holding percentage of 0.01 to 4.0 mass % and a weight-average molecular weight of less than 1,000.

Advantageous Effects of Invention

The nonwoven fabric for an absorbent article top sheet according to this disclosure has low stickiness and is light after absorption of menstrual blood, and also has low diffusion of absorbed menstrual blood on the nonwoven fabric.

DESCRIPTION OF EMBODIMENTS

Figure 1:
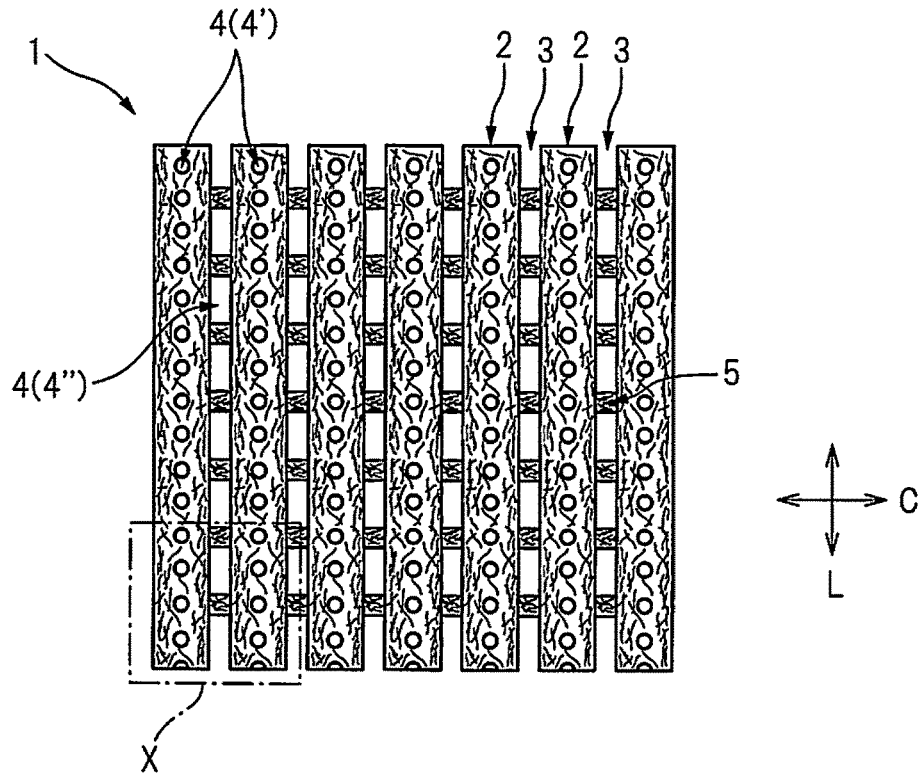
FIG. 1 is a front view of a nonwoven fabric according to an embodiment of the disclosure.

The absorbent article of this disclosure will now be explained in detail.

[Definitions]

Some of the terms used throughout the present specification will now be defined.

"Ridge" and "Furrow"

Throughout the present specification, "ridge" means a section extending basically in the longwise direction and higher than the other regions and "furrow" means a section extending basically in the longwise direction and lower than the other regions, with "ridges" and "furrows" being disposed alternately in the crosswise direction.

Throughout the present specification, the "ridges" and "furrows" are distinguished by their basis weights, for convenience.

The ridges are sections having a higher basis weight than the average basis weight of the nonwoven fabric as a whole, and the furrows are sections having a lower basis weight than the average basis weight of the nonwoven fabric as a whole.

"Fibers Oriented in the Longwise Direction"

Throughout the present specification, "fibers oriented in the longwise direction" means fibers oriented in a range of >−45° and <+45° with respect to the longwise direction. The "fibers oriented in the longwise direction" may be referred to herein as "longwisely oriented fibers".

"Fibers Oriented in the Crosswise Direction"

Throughout the present specification, "fibers oriented in the crosswise direction" means fibers oriented in a range of >−45° and <+45° with respect to the crosswise direction, which is perpendicular to the aforementioned longwise direction. The "fibers oriented in the crosswise direction" may be referred to herein as "crosswisely oriented fibers".

Fibers oriented at −45° or +45° with respect to the longwise direction (i.e. fibers also oriented at −45° or +45° with respect to the crosswise direction) are not included among either longwisely oriented fibers or crosswisely oriented fibers.

"Through-Hole"

As used herein, a "through-hole" in a nonwoven fabric is a hole running from the nonwoven fabric side (for example, the skin contact surface of the top sheet) to the opposite side (for example, the clothing side surface of the top sheet). Body fluid, such as menstrual blood that has reached the nonwoven fabric side (for example, the skin contact surface of the top sheet) can migrate to the opposite side (for example, the clothing side surface of the top sheet) through the through-holes.

The through-holes can be formed in the ridges and/or the furrows. The through-holes are not particularly limited so long as they have this function, and for example, they may be perforated sections formed by a perforation method, or openings formed by reducing the fibers of the nonwoven fabric in prescribed regions. The perforated sections and openings can be formed in the ridges and/or the furrows.

"Excretory Opening Contact Region"

As used herein, "excretory opening contact region" as it relates to the top sheet means the region of the top sheet that contacts with the excretory opening (labia minora, etc.) of the wearer. The excretory opening contact region will have a different location depending on the size of the absorbent article, and for an absorbent article with side flaps, the excretory opening contact region will usually be the inner side of the region defined by embossing disposed in a continuous or discontinuous manner surrounding a lengthwise line running through the widthwise center of the absorbent article, and the intersection with a widthwise line running through the lengthwise centers of both wing sections. Also, in the case of an absorbent article without side flaps, usually the excretory opening contact region is defined by embossing that is disposed continuously or discontinuously surrounding the widthwise center section and the lengthwise center section of the absorbent article.

The nonwoven fabric for an absorbent article top sheet according to the present disclosure will now be described in detail.

The term "nonwoven fabric for an absorbent article top sheet" may also be referred to hereunder simply as "nonwoven fabric".

Figure 2:
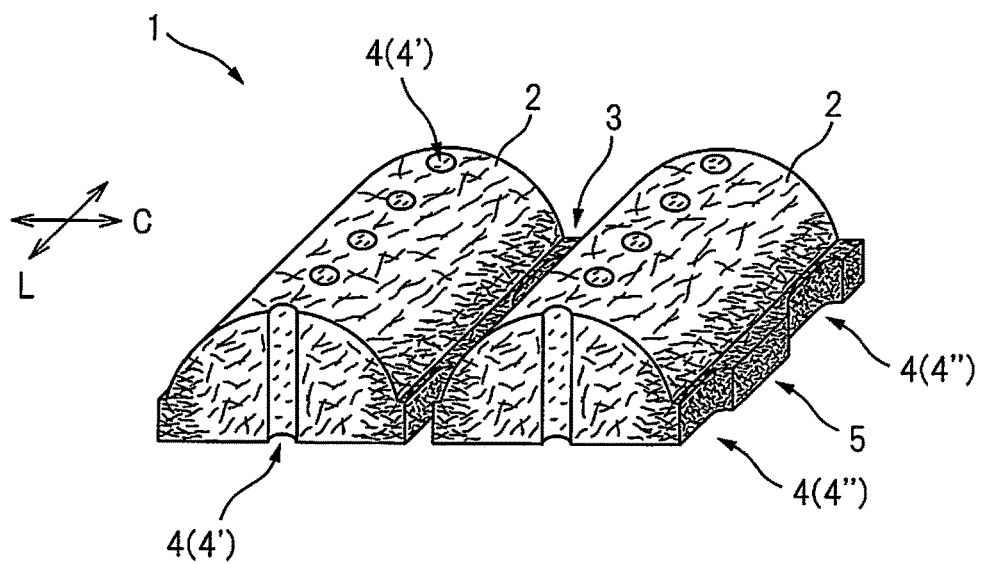
FIG. 2 is a perspective view of section X of FIG. 1.

FIG. 1 is a front view of a nonwoven fabric according to an embodiment of the disclosure, and FIG. 2 is a perspective view of section X of FIG. 1. The nonwoven fabric 1 shown in FIG. 1 and FIG. 2 has a longwise direction L and a crosswise direction C. The nonwoven fabric 1 shown in FIG. 1 and FIG. 2 has a plurality of ridges 2 and a plurality of furrows 3 extending in the longwise direction L and alternately disposed in the crosswise direction C, the ridges 2 and furrows 3 each having a plurality of through-holes 4.

In the nonwoven fabric 1 shown in FIG. 1 and FIG. 2, the through-holes 4 of the ridges 2 are a plurality of perforated sections 4' formed by perforationg, and the through-holes 4 of the furrows 3 are openings 4" formed by reducing the amount of fibers at the furrows 3 during production of the nonwoven fabric, before coating the blood slipping agent. The perforation method and the method for producing the nonwoven fabric before coating of the blood slipping agent will be described below. Furthermore, in the nonwoven fabric 1 shown in FIG. 1 and FIG. 2, the furrows 3 have joints 5 between every two adjacent openings 4", that connect every two adjacent ridges 2.

In the nonwoven fabric 1 shown in FIG. 1 and FIG. 2, the content of fibers oriented in the crosswise direction C is higher than the content of fibers oriented in the longwise direction L, at the joints 5. The nonwoven fabric 1 shown in FIG. 1 and FIG. 2 has about 0.5 to about 5.0 through-holes 4 per 1 $cm^2$ area of the nonwoven fabric 1.

In the nonwoven fabric 1 shown in FIG. 1 and FIG. 2, the ridges 2 have blood slipping agent-containing regions containing a blood slipping agent having a kinematic viscosity of about 0.01 to about 80 $mm^2/s$ at 40° C., a water holding percentage of about 0.01 to about 4.0 mass % and a weight-average molecular weight of less than 1,000. Also in the nonwoven fabric 1 shown in FIG. 1 and FIG. 2, the ridges 2 contain a blood slipping agent with a basis weight of about 1 to about 30 $g/m^2$ in the blood slipping agent-containing regions.

The blood slipping agent will be described below.

Figure 3:
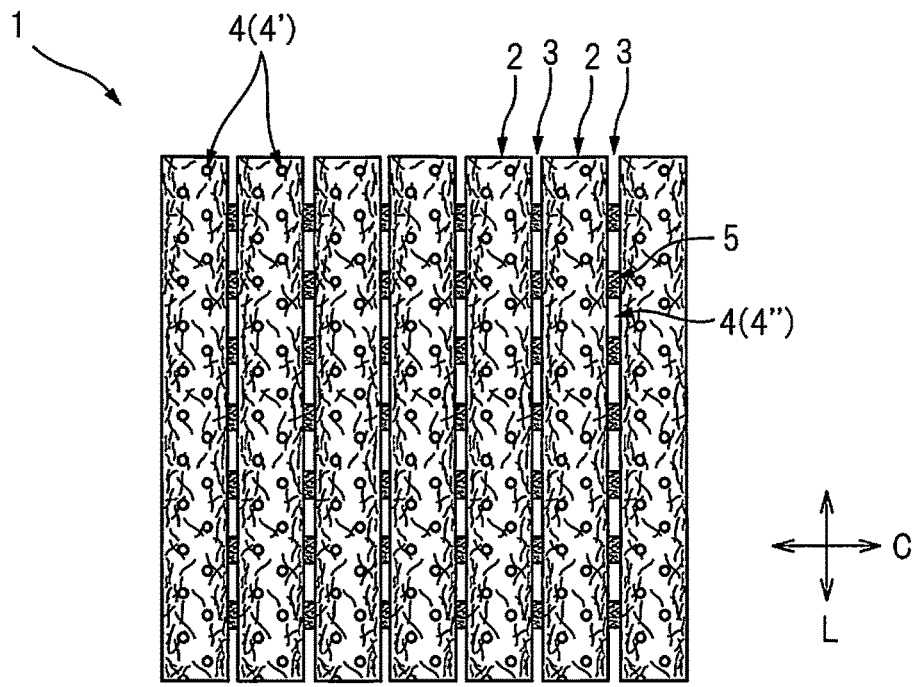
FIG. 3 is a front view of a nonwoven fabric according to another embodiment of the disclosure.

FIG. 3 is a front view of another embodiment of the nonwoven fabric of the disclosure. The nonwoven fabric 1 shown in FIG. 3 has a longwise direction L and a crosswise direction C, and a plurality of ridges 2 and a plurality of furrows 3 extending in the longwise direction L and alternately disposed in the crosswise direction C. In the nonwoven fabric 1 shown in FIG. 3, the ridges 2 and the furrows 3 each have a plurality of through-holes 4.

In the nonwoven fabric 1 shown in FIG. 3, the through-holes 4 of the ridges 2 are perforated sections 4' formed by perforation, and the perforated sections 4' of the ridges 2 are disposed in a zigzag fashion. The through-holes 4 of the furrows 3 are openings 4" formed during production of the nonwoven fabric before coating of the blood slipping agent. Furthermore, in the nonwoven fabric 1 shown in FIG. 3, the furrows 3 have joints 5 between every two adjacent openings 4", that connect every two adjacent ridges 2.

Figure 4:
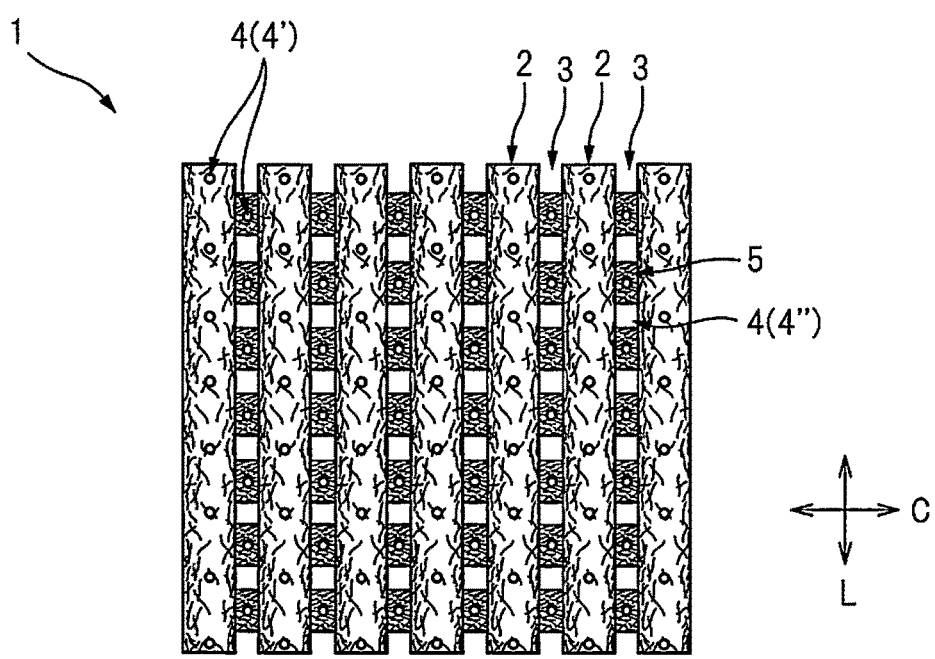
FIG. 4 is a front view of a nonwoven fabric according to yet another embodiment of the disclosure.

FIG. 4 is a front view of yet another embodiment of the nonwoven fabric of the disclosure. The nonwoven fabric 1 shown in FIG. 4 has a longwise direction L and a crosswise direction C, and a plurality of ridges 2 and a plurality of furrows 3 extending in the longwise direction L and alternately disposed in the crosswise direction C. In the nonwoven fabric 1 shown in FIG. 4, the ridges 2 and the furrows 3 each have a plurality of through-holes 4.

In the nonwoven fabric 1 shown in FIG. 4, the through-holes 4 of the ridges 2 are perforated sections 4' formed by perforation. The through-holes 4 of the furrows 3 includes both perforated sections 4' and openings 4" formed during production of the nonwoven fabric before coating of the blood slipping agent. In the nonwoven fabric 1 shown in FIG. 4, the furrows 3 have joints 5 between every two adjacent openings 4", that connect every two adjacent ridges 2.

Throughout the present specification, the contents of longwisely oriented fibers and crosswisely oriented fibers are those measured in the following manner.

(1) A digital microscope is prepared. The digital microscope may be, for example, a VHX-100 Digital Microscope by Keyence Corp.

(2) The sample to be measured is set on the observation stage so that the longwise direction and crosswise direction are clearly identifiable.

(3) Fibers irregularly protruding forward are removed from the sample to be measured, and the lens is focused on the foremost fibers of the sample.

(4) The photographing depth is set and a 3D image of the sample is displayed on a PC screen.

(5) The photographed 3D image is converted to a 2D image.

(6) Within the measuring range, multiple parallel lines are drawn on the screen in the longwise direction and the crosswise direction, dividing it into equal portions.

(7) In each cell formed by the parallel lines, measurement is made of the number of fibers oriented in the longwise direction, the number of fibers oriented in the crosswise direction, and the number of fibers not oriented in either direction.

(8) The content of longwisely oriented fibers and the content of crosswisely oriented fibers are calculated from the total number of fibers in the prescribed range.

In a nonwoven fabric according to the disclosure, the ridges have a basis weight of preferably about 15 to about 250 g/m² and more preferably about 20 to about 120 g/m². If the basis weight is less than about 15 g/m², the ridges will tend to be highly collapsable and absorbed menstrual blood will tend to rewet when pressure is applied. If the basis weight is greater than about 250 g/m², menstrual blood will not easily migrate downward (into the absorbent body, for example), and the menstrual blood will pool in the ridges, potentially creating a feeling of discomfort for the wearer.

In a nonwoven fabric according to the disclosure, the furrows have a basis weight of preferably about 3 to about 150 g/m² and more preferably about 5 to 80 g/m². If the basis weight is less than about 3 g/m², the strength of the furrows may be inadequate resulting in damage when it is used as a top sheet. Also, if the basis weight is greater than about 150 g/m², menstrual blood that has reached the furrows will not easily migrate downward (into the absorbent body), and the menstrual blood will pool in the furrows, potentially creating a feeling of discomfort for the wearer.

In a nonwoven fabric according to the disclosure, the average basis weight is preferably about 10 to 200 g/m² and more preferably about 20 to about 100 g/m². If the average basis weight is less than about 10 g/m², the strength of the nonwoven fabric may be inadequate resulting in damage when it is used as a top sheet. Also, if the average basis weight is greater than about 200 g/m², menstrual blood can potentially pool in the nonwoven fabric.

The basis weights of the ridges and the furrows and the average basis weight of the nonwoven fabric are measured in the following manner.

(1) A mark is created in the region to be measured (ridge, furrow or nonwoven fabric), and the area: $SA_\alpha(m^2)$ is measured.

In order to minimize error, marking is made so that the total area of the sample exceeds 5 cm².

(2) The marked area is cut with a sharp blade, such as a cutter replacement blade, and the total mass measured as TM(g).

(3) The basis weight $BS_\alpha(g/m^2)$ of the area to be measured is determined by the following formula:

$$BS_\alpha(g/m^2)=TM(g)/SA_\alpha(m^2).$$

In the nonwoven fabric of this disclosure, the blood slipping agent-containing regions of the ridges contain the blood slipping agent at a basis weight in the range of preferably about 1 to about 30 g/m², more preferably about 2 to about 20 g/m² and even more preferably about 3 to about 10 g/m². The action of the blood slipping agent will be described below, but if the basis weight is lower than about 1 g/m², menstrual blood that has reached the nonwoven fabric will tend to remain there without rapidly migrating into the absorbent body, while if the basis weight is greater than about 30 g/m², a greater degree of stickiness will tend to be felt when the article is worn.

Also, if the ridges region contain a blood slipping agent, menstrual blood that has reached the ridges will tend to slip down into the absorbent article before diffusing in the longwise direction along the longwisely oriented fibers. This reduces reddening of the top sheet with menstrual blood, minimizes rash caused by menstrual blood adhering to the skin, and reduces repulsive appearance.

In the nonwoven fabric of the disclosure, the furrows may also have blood slipping agent-containing regions that contain a blood slipping agent. If the furrows have blood slipping agent-containing regions, absorbed menstrual blood will easily slip into the absorbent article before diffusing in the crosswise direction. This will minimize reddening of the top sheet by menstrual blood.

For the purpose of the present specification, the basis weight of the blood slipping agent in the nonwoven fabric is that measured in the following manner.

(1) The region of the nonwoven fabric that is to be measured is cut out using a sharp blade, such as a cutter replacement blade, avoiding any alteration in thickness, to obtain a sample.

(2) The area of the sample: $SA_\beta(m^2)$ and the mass: $SM_0$ (g) are measured.

(3) The sample is stirred for at least 3 minutes in a solvent that can dissolve the blood slipping agent, such as ethanol or acetone, to dissolve the blood slipping agent in the solvent.

(4) The sample is filtered on mass-measured filter paper, and the sample is thoroughly rinsed with the solvent on the filter paper. The sample on the filter paper is dried in an oven at 60° C.

(5) The masses of the filter paper and sample are measured, and the mass of the filter paper is subtracted to calculate the dry sample mass: $SM_1$ (g).

(6) The basis weight $BS_\beta(g/m^2)$ of the blood slipping agent is calculated by the following formula.

$$BS_\beta(g/m^2)=[SM_0(g)-SM_1(g)]/SA_\beta(m^2).$$

In order to minimize error, multiple samples are taken from multiple absorbent articles, without the total area of the sample exceeding 100 cm², conducting several repeated measurements and taking the average value.

Providing a plurality of through-holes in the ridges (especially a plurality of perforated sections in the ridges) in the nonwoven fabric of the disclosure:

maintains (1) faster migration of menstrual blood reaching the nonwoven fabric (migration from the skin contact surface of the top sheet to the clothing side surface of the top sheet), and (2) flexiblity due to the bulk of the ridges, while also (3) further improving the absorption performance, and specifically (3a) inhibiting residue of menstrual blood in the ridges (since the ridges have through-holes), (3b) allowing the through-holes of the ridges to function as temporary retaining spaces for menstrual blood, and (3c) allowing menstrual blood that has reached the ridges to be guided to the through-holes along the slopes of the ridges (since formation of through-holes and especially perforated sections in the ridges reduces the thickness of the ridges around the through-holes and creates slopes in the ridges), while also (4) inhibiting mustiness (since the contact area between the ridges and the skin is reduced).

In the nonwoven fabric of the disclosure, the ridges and/or furrows have through-hole diameters of preferably about 0.3 mm to about 6.0 mm and more preferably about 0.6 mm to about 3.0 mm. If the diameters are smaller than about 0.3 mm, the through-holes that serve as fluid channels will be less conductive of highly viscous menstrual blood. If the diameters are larger than about 6.0 mm, menstrual blood that has already migrated into the absorbent body may return through the through-holes.

In the nonwoven fabric of the disclosure, the number of through-holes in the nonwoven fabric as a whole, and in the ridges and furrows, as well as the placement of the through-holes, may be appropriately selected depending on the size of the absorbent article, but at least for use as an absorbent article, the through-holes are preferably situated in the location where the excretory opening contact region is to be formed.

Generally speaking, the nonwoven fabric as a whole, and/or the ridges and/or furrows have preferably about 0.5 to about 5.0 and more preferably about 1.0 to about 3.0 through-holes per 1 cm² area of the nonwoven fabric. If this number is less than about 0.5, it may be difficult to exhibit the effect of the present disclosure, while if the number is greater than about 5.0, problems such rewetting may occur, in which menstrual blood that has already been absorbed returns back to the top sheet.

The area of the nonwoven fabric for the number of through-holes, as referred to herein, is the projected area from the thickness direction of the nonwoven fabric, and it differs from the surface area of the nonwoven fabric that includes the ridges and furrows.

In the nonwoven fabric of the disclosure, the heights of the ridges are preferably about 0.1 to about 15.0 mm higher, more preferably about 0.5 to about 5.0 mm higher and even more preferably about 0.5 to about 2.0 mm higher than the heights of the furrows. The pitch of the ridges is preferably about 1.5 to about 17 mm, more preferably about 2.0 to about 12 mm and even more preferably about 3 to about 8 mm. This is so that menstrual blood will slide down from the projections to the recesses and then rapidly migrate into the absorbent body.

The heights of the ridges and the furrows are measured by a laser displacement meter. An example of a laser displacement meter is the LJ-G Series high precision two-dimensional laser displacement gauge (Model: LJ-G030) by Keyence Corp.

In a nonwoven fabric according to one embodiment of the present disclosure, having blood slipping agent-containing regions in the furrows, the ridges and the furrows each contain the same blood slipping agent, or the same combination of blood slipping agents, in the blood slipping agent-containing regions.

Also, in a nonwoven fabric according to another embodiment of the present disclosure, which has blood slipping agent-containing regions in the furrows, the ridges and optionally the furrows each contain a different blood slipping agent, or a different combination of blood slipping agents, in the blood slipping agent-containing regions.

[Blood Slipping Agent]

In the nonwoven fabric of the disclosure, the ridges have blood slipping agent-containing regions containing a blood slipping agent having a kinematic viscosity of about 0.01 to about 80 mm²/s at 40° C., a water holding percentage of about 0.05 to about 4.0 mass % and a weight-average molecular weight of less than 1,000.

The blood slipping agent has, at 40° C., a kinematic viscosity of about 0 to about 80 mm²/s, preferably a kinematic viscosity of about 1 to about 70 mm²/s, more preferably a kinematic viscosity of about 3 to about 60 mm²/s, even more preferably a kinematic viscosity of about 5 to about 50 mm²/s, and yet more preferably a kinematic viscosity of about 7 to about 45 mm²/s.

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm²/s at 40° C., the melting point of the blood slipping agent is preferably 45° C. or less. This is because the kinematic viscosity will tend to be higher if the blood slipping agent contains crystals at 40° C.

As used herein, the "kinematic viscosity at 40° C." may be referred to simply as "kinematic viscosity".

The significance of the kinematic viscosity of the blood slipping agent will be explained below, but a kinematic viscosity exceeding about 80 mm²/s will tend to result in high viscosity of the blood slipping agent, so that the blood slipping agent will tend to be resistant to slipping into the absorbent article together with menstrual blood that has reached the skin contact surface of the top sheet.

The kinematic viscosity can be measured according to JIS K 2283:2000, "5. Kinematic Viscosity Test Method", using a Cannon-Fenske reverse-flow viscometer, at a testing temperature of 40° C.

The blood slipping agent has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

As used herein, "water holding percentage" means the percentage (mass) of water that can be held by a substance, and it may be measured in the following manner.

(1) A 20 mL test tube, a rubber stopper, the substance to be measured and deionized water are allowed to stand for a day and a night in a thermostatic chamber at 40° C.

(2) Into the test tube in the thermostatic chamber there are charged 5.0 g of the substance to be measured and 5.0 g of deionized water.

(3) The mouth of the test tube is sealed with the rubber stopper in the thermostatic chamber, and the test tube is rotated once and allowed to stand for 5 minutes.

(4) A 3.0 g portion of the layer of the substance to be measured (usually the upper layer) is sampled into a glass dish with a diameter of 90 mm and a mass of $W_0$ (g), in the thermostatic chamber.

(5) The dish is heated at 105° C. for 3 hours in an oven to evaporate off the moisture, and the mass $W_1$ (g) of each dish is measured.

(6) The water holding percentage is calculated by the following formula.

$$\text{Water holding percentage (mass \%)} = 100 \times [W_0(g) - W_1(g)] / 3.0(g)$$

The measurement is conducted three times, and the average value is recorded.

The significance of the water holding percentage of the blood slipping agent will be explained below, but a low water holding percentage will tend to lower the affinity between the blood slipping agent and menstrual blood, thus helping to prevent menstrual blood that has reached the skin contact surface of the top sheet from slipping into the absorbent article.

If the water holding percentage is high, on the other hand, affinity with menstrual blood will be very high, similar to a surfactant, and absorbed menstrual blood will tend to remain on the skin contact surface of the top sheet, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e with a higher inorganic value or with a lower organic value. This is because the blood slipping agent will have greater hydrophilicity.

The significance of the kinematic viscosity and water holding percentage of the blood slipping agent will now be explained.

Figure 5:
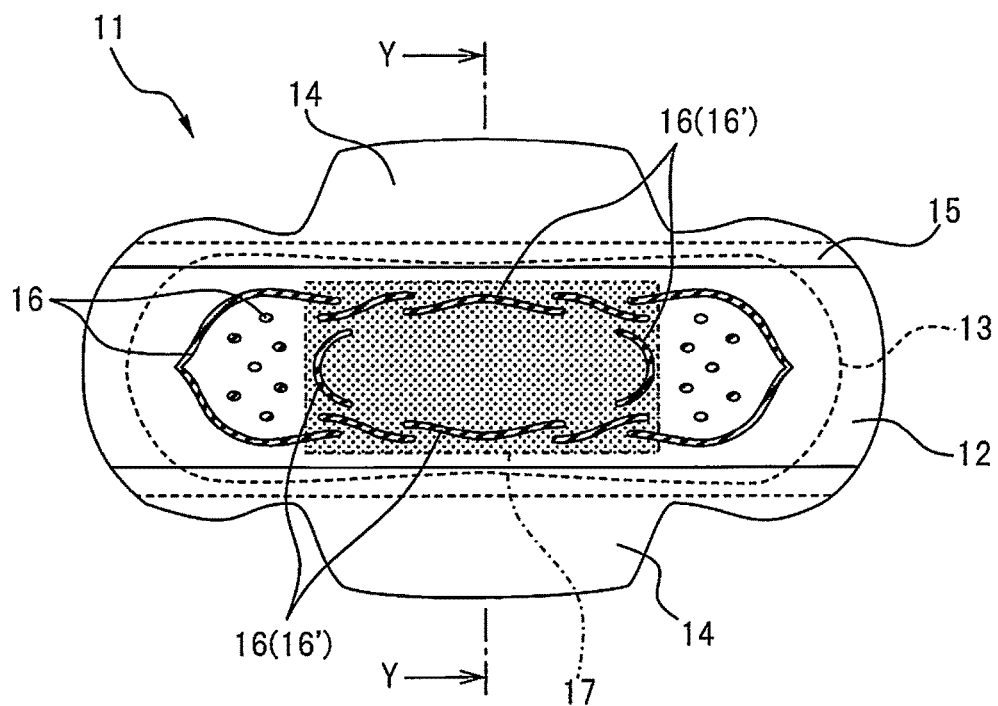
FIG. 5 is a front view of an absorbent article 11 comprising a nonwoven fabric, according to the disclosure.

FIG. 5 is a front view of an absorbent article, and more specifically a sanitary napkin, containing a nonwoven fabric of the disclosure. FIG. 5 is as observed from the skin contact side of the top sheet 12. The absorbent article 11 shown in FIG. 5 has a liquid-permeable top sheet 12, an absorbent body 13, and a liquid-impermeable back sheet (not shown). The absorbent article 11 shown in FIG. 5 also has a pair of side flaps 14, a side sheet 15 and embossings 16.

In the absorbent article 11 shown in FIG. 5, the left side is the front.

In the absorbent article 11 shown in FIG. 5, the top sheet 12 has a plurality of ridges and a plurality of furrows on the skin contact surface, extending in the lengthwise direction of the absorbent article, and the ridges and furrows may be omitted as appropriate. In the absorbent article 11 shown in FIG. 5, the ridges and furrows are disposed in an alternating fashion in the widthwise direction of the absorbent article 11.

Also, although the absorbent article 11 shown in FIG. 5 has a pair of side flaps 14, a side sheet 15 and embossings 16, an absorbent article according to another embodiment of this disclosure does not have a pair of side flaps, a side sheet and/or embossings.

In the absorbent article 11 shown in FIG. 5, the excretory opening contact region is the region defined by four embossings 16', and the top sheet 12 has a blood slipping agent-containing region 17 over the entire excretory opening contact region.

Figure 6:
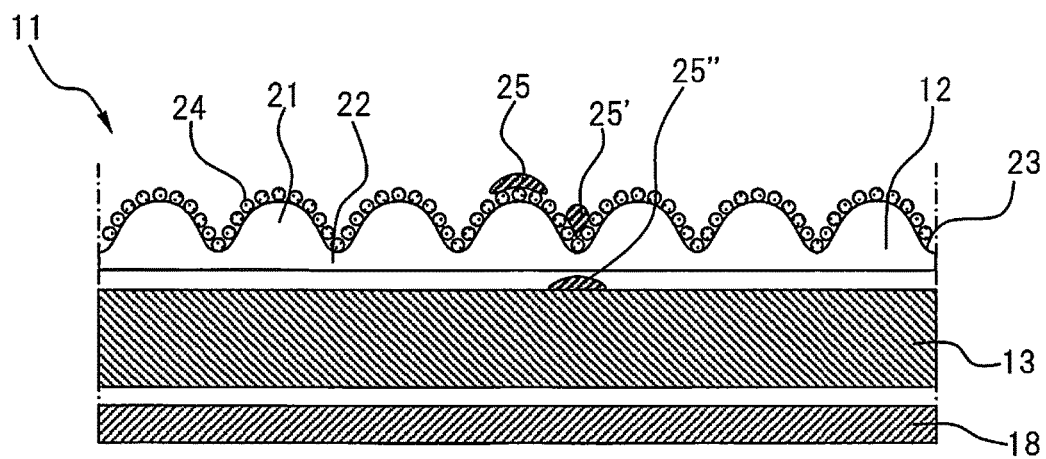
FIG. 6 is a cross-sectional view of the blood slipping agent-containing region 17 of the absorbent article 11 shown in FIG. 3, along cross-section Y-Y.

FIG. 6 is a cross-sectional view corresponding to cross-section Y-Y of the blood slipping agent-containing region 17 of the absorbent article 11 shown in FIG. 5, and it is a diagram schematically illustrating migration of menstrual blood into the absorbent body by the blood slipping agent. The absorbent article 11 shown in FIG. 6 has a liquid-permeable top sheet 12, a liquid-impermeable back sheet 18, and an absorbent body 13 between the top sheet 12 and the back sheet 18.

In FIG. 6, the top sheet 12 has a plurality of projections 21 and a plurality of recesses 22 on the skin contact surface 23, and a blood slipping agent 24 is coated on the skin contact surface 23 of the top sheet 12. In FIG. 6, the blood slipping agent 24 is shown as droplets (or particles) on the skin contact surface 23 of the top sheet 12 for convenience, but in a nonwoven fabric of this disclosure, and an absorbent article comprising the nonwoven fabric, the form and distribution of the blood slipping agent is not limited to that shown in the drawing.

As shown in FIG. 6, menstrual blood 25 that has reached the projections 21 of the top sheet 12 contacts with the blood slipping agent 24 that is present in the projections 21. A portion of the blood slipping agent 24 present in the projections 21 slips down into the recesses 22 together with the menstrual blood 25 (menstrual blood 25'). The menstrual blood 25' then slips down into the recesses 22, reaching the absorbent body 13 (menstrual blood 25''). Next, the menstrual blood 25'' is absorbed into the absorbent body 13.

More specifically, the blood slipping agent 24 having a water holding percentage of about 0.01 to about 4.0 mass % has a certain affinity with menstrual blood 25. For example, the hydrophilic portion of the blood slipping agent 24 (for example, a hydrophilic group, such as a polar group, for example, such as carbonyl, oxy, carboxyl, hydroxyl or the like, or a hydrophilic bond, such as a polar bond, for example, such as a carbonyl bond, ester bond, carbonate bond, ether bond or the like) has high affinity with the hydrophilic components (such as blood plasma) in the menstrual blood 25, and attracts the components with affinity, whereas the hydrophobic portion (for example, the hydrocarbon moiety) of the blood slipping agent 24 has low affinity with the hydrophilic components (such as blood plasma) in the menstrual blood 25 and repels the hydrophilic components, such that it functions as a "lubricant", causing the menstrual blood 25 to slip down toward the absorbent body 13.

Also, since the blood slipping agent 24 having a kinematic viscosity of about 0.01 to about 80 mm$^2$/s at 40° C. has very low viscosity near the body temperature of the wearer, a portion thereof slips down from the projections 21 into the recesses 22 together with the menstrual blood 25, subsequently passing through the recesses 22 into the absorbent article 11.

Furthermore, since the blood slipping agent 24 has a water holding percentage of about 0.01 to about 4.0 mass %, its affinity with the hydrophilic components (such as blood plasma) in menstrual blood 25 is not excessively high, and this causes less of the menstrual blood 25 to remain on the top sheet 12. This is because the hydrophilic components (such as blood plasma) in the menstrual blood 25 repels the hydrophobic portion of the blood slipping agent 24.

Also, FIG. 6 schematically illustrates migration of menstrual blood into an absorbent body by a blood slipping agent, but a blood slipping agent-containing composition functions in the same manner.

The blood slipping agent has a weight-average molecular weight of less than about 1,000, and preferably a weight-average molecular weight of less than about 900. This is because, if the weight-average molecular weight is about 1,000 or higher, tack may result in the blood slipping agent itself, tending to create a feeling of unpleasantness for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

In addition, as used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF

Flow rate: 1.0 mL/min

Driving volume: 100 μL

Detection: RI (differential refractometer)

The weight-average molecular weights listed in the examples of the present specification were measured under the conditions described below.

The blood slipping agent can have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of no higher than 45° C., and more preferably it has a melting point of no higher than 40° C. If the blood slipping agent has a melting point of no higher than 45° C., the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The differential scanning calorimetry analyzer used may be, for example, a DSC-60-type DSC measuring apparatus by Shimadzu Corp.

If the blood slipping agent has a melting point of about 45° C. or less, it may be either liquid or solid at room temperature (about 25° C.), or in other words, the melting point may be either about 25° C. or higher or below about 25° C., and for example, it may have a melting point of about −5° C. or about −20° C.

The blood slipping agent does not have a lower limit for the melting point, but the vapor pressure is preferably low. The vapor pressure of the blood slipping agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the nonwoven fabric of this disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood slipping agent may be reduced, and as a consequence problems, such as odor during wear, may be created.

The melting point of the blood slipping agent may be selected depending on the weather or duration of wear. For example, in regions with a mean atmospheric temperature of about 10° C. or less, using a blood slipping agent with a melting point of about 10° C. or less may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less: This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

Preferably, the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen on the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

More preferably, the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent has more preferably about 1.8 or less carbonyl bonds (—CO—), about 2 or less ester bonds (—COO—), about 1.5 or less carbonate bonds (—OCOO—), about 6 or less ether bonds (—O—), about 0.8 or less carboxyl groups (—COOH) and/or about 1.2 or less hydroxyl groups (—OH), per 10 carbon atoms in the hydrocarbon moiety.

Even more preferably, the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or ester or ether thereof; and (F) a chain hydrocarbon.

The blood slipping agent in accordance with (A) to (F) will now be described in detail.

[(A) Ester of (A1) a Compound Having a Chain Hydrocarbon Moiety and 2-4 Hydroxyl Groups Substituting for Hydrogens on the Chain Hydrocarbon Moiety, and (A2) a Compound Having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

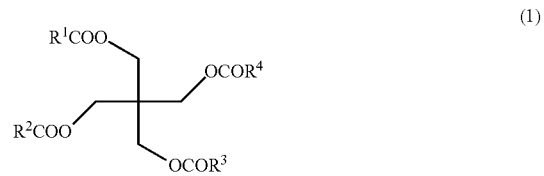

triesters of pentaerythritol and fatty acids, represented by the following formula (2):

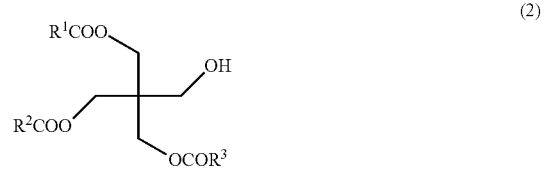

diesters of pentaerythritol and fatty acids, represented by the following formula (3):

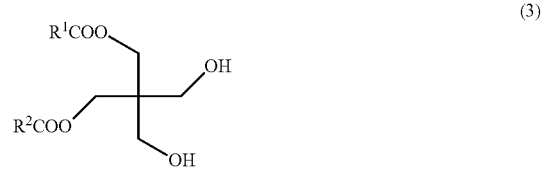

and monoesters of pentaerythritol and fatty acids, represented by the following formula (4).

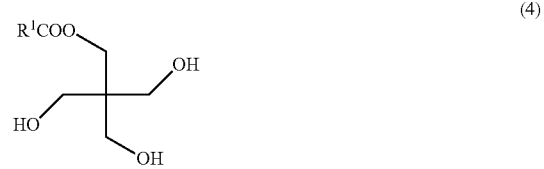

In the formulas, $R^1$-$R^4$ each represent a chain hydrocarbon.

The fatty acids consisting of the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof, such as 2-methylpropanoic acid ($C_4$), pentanoic acid ($C_5$) and isomers thereof, such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers thereof which are not described above.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts thereof.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, from the viewpoint of lowering the water holding percentage, the ester of pentaerythritol and a fatty acid is preferably a diester, triester or tetraester, more preferably a triester or tetraester, and even more preferably a tetraester.

From the viewpoint of the IOB being from about 0.00 to about 0.60, in a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_8$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

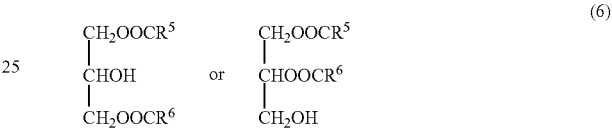

and monoesters of glycerin and fatty acids, represented by the following formula (7):

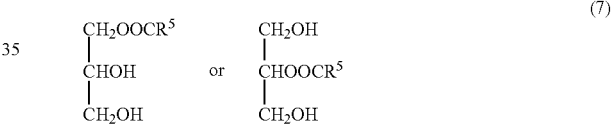

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, from the viewpoint of lowering the water holding percentage and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or 3 different fatty acids, and mixtures threreof.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with about 40 or less as the total number of carbons of the fatty acid consisting of the triester of glycerin and the fatty acid, i.e., the total number of carbons of the $R^5C$, $R^6C$ and $R^7C$ sections in formula (5).

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures thereof.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon,
and monoesters of $C_2$-$C_6$ glycols and fatty acids, represented by the following formula (9):

$$R^8COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

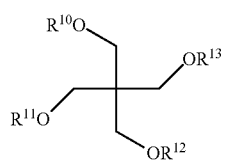

(10)

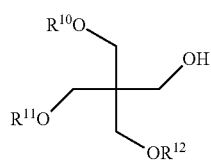

(11)

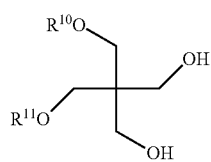

(12)

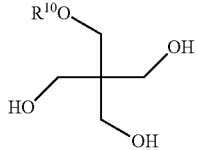

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ | \\ CHOR^{15} \\ | \\ CH_2OR^{16} \end{array} \quad (14)$$

$$\begin{array}{l} CH_2OR^{14} \\ | \\ CHOH \\ | \\ CH_2OR^{15} \end{array} \quad or \quad \begin{array}{l} CH_2OR^{14} \\ | \\ CHOR^{15} \\ | \\ CH_2OH \end{array} \quad (15)$$

$$\begin{array}{l} CH_2OR^{14} \\ | \\ CHOH \\ | \\ CH_2OH \end{array} \quad or \quad \begin{array}{l} CH_2OH \\ | \\ CHOR^{14} \\ | \\ CH_2OH \end{array} \quad (16)$$

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, (d$_2$) a dialkyl ketone, (d$_3$) an ester of a fatty acid and an aliphatic monohydric alcohol, or (d$_4$) a dialkyl carbonate.

[(d$_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \quad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[(d$_2$) Dialkyl Ketone]

The dialkyl ketone may be a compound of the following formula (20):

$$R^{21}COR^{22} \quad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[(d$_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \quad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "(a$_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid (C$_{12}$) and dodecyl alcohol (C$_{12}$) and esters of tetradecanoic acid (C$_{14}$) and dodecyl alcohol (C$_{12}$), and examples of commercial products of esters of such fatty acids and aliphatic monohydric alcohols include ELECTOL WE20 and ELECTOL WE40 (both products of NOF Corp.).

[(d$_4$) Dialkyl Carbonate]

The dialkyl carbonate may be a compound of the following formula (22):

$$R^{25}OC(=O)OR^{26} \quad (22)$$

wherein $R^{25}$ and $R^{26}$ are each an alkyl group.

The dialkyl carbonate may be a commercially available product, or it may be synthesized by reaction between phosgene and an alcohol, reaction between formic chloride and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for (d$_1$) an ether of an aliphatic monohydric alcohol and an aliphatic monohydric alcohol, (d$_2$) a dialkyl ketone, (d$_3$) an ester of a fatty acid and an aliphatic monohydric alcohol, and (d$_4$) a dialkyl carbonate.

If the total number of carbon atoms is about 8 in a (d$_2$) dialkyl ketone, the melting point will be approximately −50° C. and the vapor pressure will be about 230 Pa at 20° C., in the case of 5-nonanone, for example.

[(E) Polyoxy C$_3$-C$_6$ Alkylene Glycol, or Alkyl Ester or Alkyl Ether Thereof]

The (E) polyoxy C$_3$-C$_6$ alkylene glycol, or alkyl ester or alkyl ether thereof (hereunder also referred to as "compound (E)") may be (e$_1$) a polyoxy C$_3$-C$_6$ alkylene glycol, (e$_2$) an ester of a polyoxy C$_3$-C$_6$ alkylene glycol and at least one fatty acid, or (e$_3$) an ether of a polyoxy C$_3$-C$_6$ alkylene glycol and at least one aliphatic monohydric alcohol. These will now be explained.

[(e$_1$) Polyoxy C$_3$-C$_6$ Alkylene Glycol]

Polyoxy C$_3$-C$_6$ alkylene glycols refer to i) homopolymers having one unit selected from the group consisting of oxy C$_3$-C$_6$ alkylene units, such as oxypropylene unit, oxybutylene unit, oxypentylene unit and oxyhexylene unit and having hydroxyl groups at both ends, ii) block copolymers having 2 or more units selected from oxy C$_3$-C$_6$ alkylene units described above and oxyhexylene unit and having hydroxyl groups at both ends, or iii) random copolymers having 2 or more units selected from oxy C$_3$-C$_6$ alkylene units described above and having hydroxyl groups at both ends.

The polyoxy C$_3$-C$_6$ alkylene glycol can be represented by the following formula (23):

$$HO-(C_mH_{2m}O)_n-H \quad (23)$$

wherein m represents an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the (e$_1$) polyoxy C$_3$-C$_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥about 7 (when n=7, the IOB is 0.57).

Examples of commercial products of poly C$_3$-C$_6$ alkylene glycols include UNIOL™ PB-500 and PB-700 (all products of NOF Corp.).

[(e$_2$) Ester of a Polyoxy C$_3$-C$_6$ Alkylene Glycol and at Least One Fatty Acid]

Examples of an ester of a polyoxy C$_3$-C$_6$ alkylene glycol and at least one fatty acids include the polyoxy C$_3$-C$_6$ alkylene glycols mentioned for "(e$_1$) Polyoxy C$_3$-C$_6$ alkylene glycol" in which one or both OH ends have been esterified with fatty acids, i.e. monoesters and diesters.

Examples of fatty acids to be esterified in the ester of a polyoxy C$_3$-C$_6$ alkylene glycol and at least one fatty acid include the fatty acids mentioned for the "(a$_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

Examples of an ether of a polyoxy $C_3$-$C_6$ alkylene glycols and at least one aliphatic monohydric alcohol include the polyoxy $C_3$-$C_6$ alkylene glycols mentioned for "($e_1$) Polyoxy $C_3$-$C_6$ alkylene glycol" wherein one or both OH ends have been etherified by an aliphatic monohydric alcohol, i.e. monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of about 45° C. or less have up to about 22 carbon atoms, and at a vapor pressure of 1 atmosphere and no greater than about 0.01 Pa at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

In a nonwoven fabric according to one embodiment of this disclosure, the ridges have blood slipping agent-containing regions that contain the aforementioned blood slipping agent. In a nonwoven fabric according to another embodiment of the disclosure, the ridges have blood slipping agent-containing regions that consist entirely of a blood slipping agent. In a nonwoven fabric according to yet another embodiment of this disclosure, the ridges have blood slipping agent-containing regions that comprise a blood slipping agent-containing composition including the aforementioned blood slipping agent and at least one other component.

In a nonwoven fabric according to one embodiment of this disclosure, the furrows have blood slipping agent-containing regions that contain a blood slipping agent. In a nonwoven fabric according to another embodiment of the disclosure, the furrows have blood slipping agent-containing regions that consist entirely of a blood slipping agent. In a nonwoven fabric according to yet another embodiment of this disclosure, the furrows have blood slipping agent-containing regions that comprise a blood slipping agent-containing composition including the aforementioned blood slipping agent and at least one other component.

Such a blood slipping agent-containing composition will now be described.

[Blood Slipping Agent-Containing Composition]

The blood slipping agent-containing composition contains a blood slipping agent and at least one other component. The other component is not particularly restricted so long as it does not inhibit the effect of the present disclosure, and it may be any one commonly employed in absorbent articles of the art, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including vitamin $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins.

The derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, *salvia* extract, linden extract, common lime extract, white birch extract, common horsetail extract, sage extract, *salvia* extract, walnut (*J. regia* L. var. *orientalis*) extract, hibiscus extract, loquat leaf extract, Miquel's linden extract, hop extract, common horsechestnut extract and *coix* seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts. Examples of anti-inflammatory components include naturally-derived anti-inflammatory drugs, such as peony, golden grass, otogiriso, chamomile, licorice, peach leaf, Japanese mugwort and *perilla* extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. These ranges are from the viewpoint of the effect of the present disclosure.

The blood slipping agent-containing composition preferably contains a surfactant in no greater than the amount from hydrophilicizing treatment of the top sheet or second sheet. More specifically, the blood slipping agent-containing composition contains a surfactant in a basis weight range of preferably about 0.0 to about 1.0 $g/m^2$, more preferably about 0.0 to about 0.8 $g/m^2$, even more preferably about 0.1 to about 0.5 $g/m^2$, and yet more preferably about 0.1 to about 0.3 $g/m^2$.

This is because when the amount of surfactant is increased, menstrual blood will tend to be retained in the top sheet. The surfactant, incidentally, has no water holding percentage. This is because there is no layer of the substance to be measured, due to admixture with water.

The blood slipping agent-containing composition contains water in a basis weight range of preferably about 0.0 to about 1.0 $g/m^2$, more preferably about 0.0 to about 0.8 $g/m^2$, even more preferably about 0.1 to about 0.5 $g/m^2$, and yet more preferably about 0.1 to about 0.3 $g/m^2$.

Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 $mm^2/s$, more preferably a kinematic viscosity of about 1 to about 70 $mm^2/s$, even more preferably a kinematic viscosity of about 3 to about 60 $mm^2/s$, yet more preferably a kinematic viscosity of about 5 to about 50 $mm^2/s$, and even yet more preferably a kinematic viscosity of about 7 to about 45 $mm^2/s$.

If the kinematic viscosity of the blood slipping agent-containing composition exceeds 80 $mm^2/s$, the viscosity will increase, and the blood slipping agent composition may not slide down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1000, and more preferably a weight-average molecular weight of less than about 900. This is because, if the weight-average molecular weight is about 1000 or higher, tack may result in the blood slipping agent-containing composition itself, tending to create a feeling of unpleasantness for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from sliding down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

The blood slipping agent or blood slipping agent-containing composition may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent or blood slipping agent-containing composition will be lowered, thereby allowing the application steps to be simplified, facilitating application and making heating during application unnecessary.

[Nonwoven Fabric and Method for Producing Absorbent Article]

The nonwoven fabric of the disclosure can be produced by a method known in the technical field. The nonwoven fabric of the disclosure can be produced, for example, according to the method described in PTL 1, by forming a nonwoven fabric that is to have through-holes formed therein and that is to be coated with a blood slipping agent, and then providing perforated sections (through-holes) in the ridges by perforation to form a nonwoven fabric that is to be coated with a blood slipping agent, and subsequently coating a blood slipping agent onto the nonwoven fabric that is to be coated with the blood slipping agent. For example, a nonwoven fabric 1 as shown in FIG. 1 to FIG. 4, prior to formation of perforated sections 4', can be produced according to the "first embodiment" in PTL 1.

When a nonwoven fabric is to be produced in a nonwoven fabric production apparatus, such as described in PTL 1, using a supporting member, such as shown in FIG. 3 of PTL 1, it is possible to produce a nonwoven fabric having a plurality of ridges and a plurality of furrows, wherein the furrows have a plurality of openings and joints connecting every two adjacent ridges between every two adjacent openings.

Figure 7:
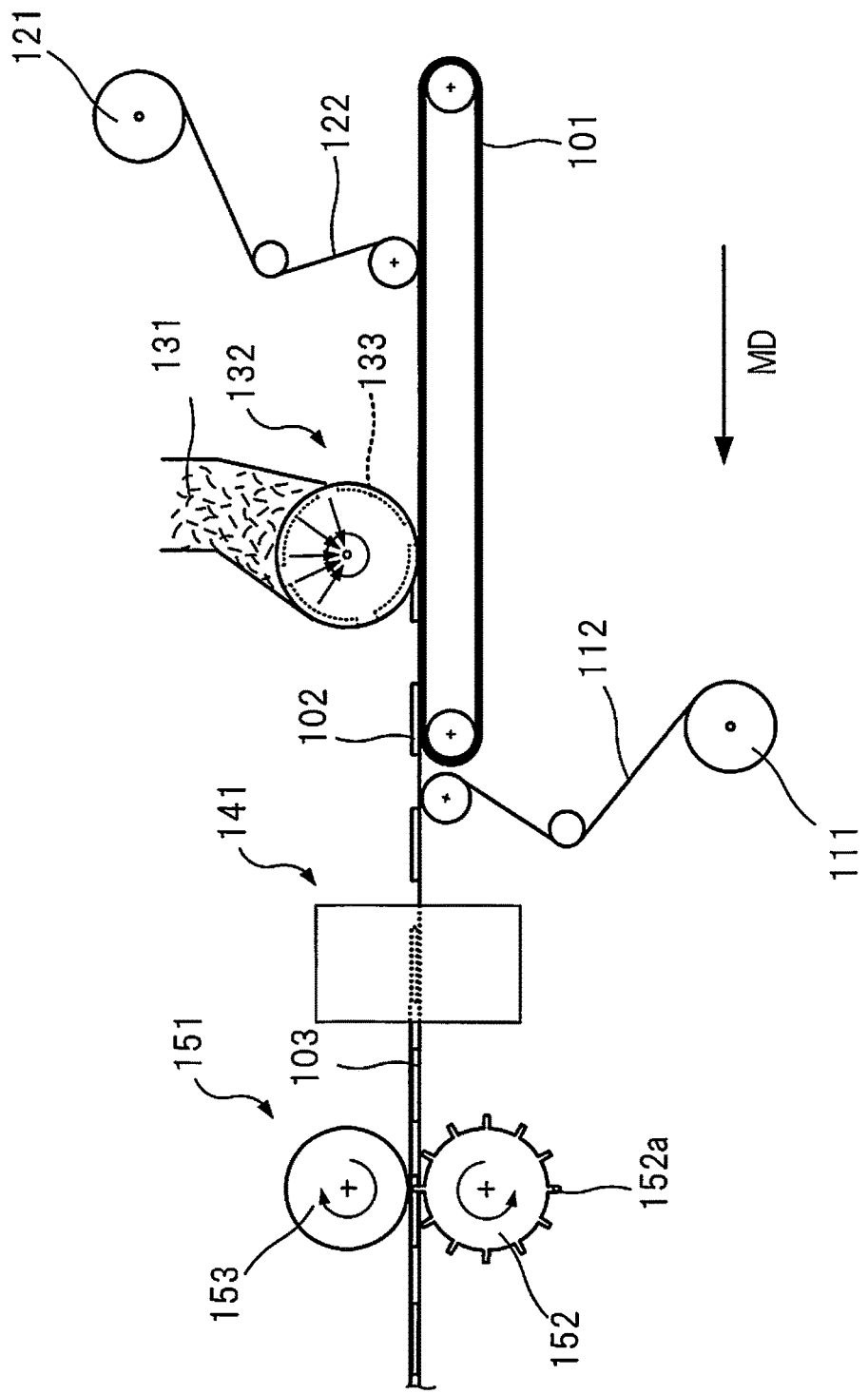
FIG. 7 is a diagram illustrating an example of a method of forming perforated sections in a nonwoven fabric sheet 102.

The perforation method may be carried out according to a method known in the technical field, but it is preferred to employ a perforation method, such as shown in FIG. 7, for example.

FIG. 7 is a diagram illustrating an example of a method of forming perforated sections.

A core wrap sheet 122 supplied from a core wrap roll 121 is transported by a belt conveyor 101 in the machine direction MD. Next, ground pulp and an absorbent polymer 131 are supplied from a ground pulp/absorbent polymer supply apparatus (not shown), to a pattern drum 132. Recesses 133 are formed around the outer periphery of the pattern drum 132, for molding of the ground pulp and the absorbent polymer. The interior of the pattern drum 132 is aspirated, so that the ground pulp and absorbent polymer 131 supplied to the pattern drum 132 are sucked into the recesses 133, and they are compacted to form an absorbent core 102. The absorbent core 102 is then layered onto the core wrap sheet 122.

Next, the nonwoven fabric sheet 112 supplied from the nonwoven fabric roll 111 is merged with the core wrap sheet 122 from below the core wrap sheet 122, and a sealer 141 is used to fold the section of the core wrap sheet 122 that is protruding to the outer side (the widthwise direction perpendicular to the machine direction MD) onto the absorbent core 102 to form an absorbent body 103 on the nonwoven fabric sheet 112.

A perforation apparatus 151 is then used to form perforated sections by perforation in the nonwoven fabric sheet 112 and absorbent body 103. The perforation apparatus 151 includes a protrusion roll 152 having a plurality of protrusions 152a with shapes, such as needle-like, cylindrical or conical shapes on the outer peripheral surface, and a plain roll 153 having a smooth surface on the outer periphery. The rotational direction of the protrusion roll 152 and the plain roll 153 is the same direction as the direction of movement of the nonwoven fabric sheet 112 and the absorbent body 103 (the machine direction MD).

The nonwoven fabric sheet 112 and the absorbent body 103 are passed between the protrusion roll 152 and the plain roll 153, to form perforated sections on the nonwoven fabric sheet 112 and depressed sections in the absorbent body 103. The perforated sections in the nonwoven fabric sheet 112 and the depressed sections in the absorbent body 103 are formed at matching locations in the thickness direction.

This method forms a nonwoven fabric that is to be coated with a blood slipping agent.

FIG. 7 shows an example wherein both the nonwoven fabric sheet 112 and the absorbent body 103 are bored simultaneously, but according to a different embodiment, a perforation apparatus, such as shown in FIG. 7 is used to bore only the nonwoven fabric and form perforated sections in the nonwoven fabric.

There are no particular restrictions on the method of applying the blood slipping agent or blood slipping agent-containing composition, or the coating solution containing it, and if necessary the blood slipping agent or blood slipping agent-containing composition or the coating solution containing it may be heated, and a coating applicator, for example a non-contact coater, such as a spiral coater, curtain coater, spray coater or dip coater, or a contact coater, may be used for application of the blood slipping agent or blood slipping agent-containing composition or the coating solution containing it. The coating applicator is preferably a non-contact coater, from the viewpoint of uniformly dispersing the droplet or particulate modifying agent throughout, and from the viewpoint of not causing damage in the material.

The blood slipping agent or blood slipping agent-containing composition, or the coating solution containing it, may be coated directly, if it is a liquid at room temperature, or it may be heated to lower the viscosity, and when it is a solid at room temperature, it may be heated to liquefaction and coated from a control seam HMA (Hot Melt Adhesive) gun. By increasing the air pressure of the control seam HMA gun, it is possible to apply the blood slipping agent or blood slipping agent-containing composition as fine particulates.

The coating amount of the blood slipping agent or blood slipping agent-containing composition may be adjusted, for example, by increasing or reducing the amount of application from the control seam HMA gun.

For example, a blood slipping agent or the like may be applied along the ridges from a control seam HMA gun to form blood slipping agent-containing regions in the ridges.

Alternatively, a blood slipping agent or the like may be applied from a control seam HMA gun onto the entire nonwoven fabric that is to be coated with the blood slipping agent, to form blood slipping agent-containing regions in the ridges and furrows.

An absorbent article including the nonwoven fabric of this disclosure can be produced by a method known in the technical field. For example, the absorbent article can be produced by layering a liquid-permeable back sheet, an absorbent body and the aforementioned nonwoven fabric with an adhesive between them, and then cutting it into an absorbent article shape.

The nonwoven fabric of the disclosure may have stamped sections formed by stamping the nonwoven fabric. If the nonwoven fabric of the disclosure has stamped sections, the blood slipping agent will slide down from the projections to the recesses, together with menstrual blood, and menstrual blood will subsequently be able to rapidly migrate into the absorbent body.

Any liquid-permeable top sheet that is commonly used in the technical field may be employed without any particular restrictions, and for example, it may be a sheet-like material having a structure that allows permeation of liquids, such as a film, woven fabric, nonwoven fabric or the like. The fibers composing such a woven fabric or nonwoven fabric may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m$^2$, for example, is preferred.

An absorbent article according to one embodiment of this disclosure includes a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations thereof. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3 to about 5.0 mm. The absorbing sheet or polymer sheet may usually be used without any particular restrictions so long as it is one that can be used in an absorbent article, such as a sanitary napkin.

The side sheet may be any of the same examples as for the liquid-permeable top sheet.

The flap can be formed from a side sheet and a liquid-impermeable back sheet, and optionally it may have a reinforcing sheet, such as paper, between them.

The blood slipping agent or blood slipping agent-containing composition preferably does not occlude the voids between the fibers of the nonwoven fabric, and the blood slipping agent or blood slipping agent-containing composition may, for example, adhere as droplets or particulates on the surfaces of the fibers of the nonwoven fabric, or it may cover the surfaces of the fibers.

Furthermore, in order for the blood slipping agent or blood slipping agent-containing composition to slip down together with the absorbed menstrual blood, it preferably has a large surface area, and a blood slipping agent or blood slipping agent-containing composition present as droplets or particulates preferably has a small droplet/particle diameter.

An absorbent article according to another embodiment of this disclosure has a second sheet containing a blood slipping agent. An absorbent article according to yet another embodiment of this disclosure has an absorbent body containing a blood slipping agent.

A nonwoven fabric coated with a blood slipping agent or blood slipping agent-containing composition is preferably subjected to hydrophilicizing treatment. The hydrophilicizing treatment may involve coating the surfaces of the fibers of the nonwoven fabric with a hydrophilic agent, or mixing a hydrophilic agent with the synthetic resin used as the starting material for the nonwoven fabric.

This is because if the nonwoven fabric before coating of the blood slipping agent or blood slipping agent-containing composition is hydrophilic, there will be lipophilic regions due to the blood slipping agent and hydrophilic regions due to the hydrophilic agent, that are sparsely dispersed on the top sheet, and this will allow the blood slipping agent or blood slipping agent-containing composition to exhibit slipping performance and will also facilitate rapid migration of menstrual blood into the absorbent body.

The blood slipping agent or blood slipping agent-containing composition also has an effect as a lubricant. Thus the blood slipping agent or blood slipping agent-containing composition reduces friction between the fibers of the nonwoven fabric, and improves the flexibility of the nonwoven fabric as a whole.

An absorbent article according to a preferred embodiment of this disclosure may be one that is intended for absorption of blood, such as a sanitary napkin or panty liner.

The nonwoven fabric of this disclosure, and the absorbent article comprising the nonwoven fabric, differ from known absorbent articles containing skin care compositions, lotion compositions and the like, in that they do not need components, such as emollients or immobilizing agents, and therefore the nonwoven fabric according to one embodiment of this disclosure, and an absorbent article comprising the nonwoven fabric, do not contain an emollient and/or immobilizing agent.

EXAMPLES

The present disclosure will now be explained in fuller detail by examples, with the understanding that it is not meant to be limited to the examples.

Example 1

[Evaluation of Rewetting Rate and Absorbent Body Migration Rate]

A commercially available sanitary napkin having the shape shown in FIG. 5 (not coated with a blood slipping agent) was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood slipping agents used for testing are listed below.

[(a$_1$) Ester of Chain Hydrocarbon Tetraol and at Least One Fatty Acid]

UNISTAR H-408BRS, Product of NOF Corp.

Pentaerythritol tetra(2-ethylhexanoate), weight-average molecular weight: approximately 640

UNISTAR H-2408BRS-22, Product of NOF Corp.

Mixture of pentaerythritol tetra(2-ethylhexanoate) and neopentylglycol di(2-ethylhexanoate) (58:42 as weight ratio), weight-average molecular weight: approximately 520

[(a$_2$) Ester of Chain Hydrocarbon Triol and at Least One Fatty Acid]

Cetiol SB45DEO, Cognis Japan

Glycerin and fatty acid triester, with oleic acid or stearylic acid as the fatty acid.

SOY42, Product of NOF Corp.

Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L Oil Fatty Acid Glyceride, Product of NOF Corp.

Glycerin and fatty acid triester with $C_8$ fatty acid:$C_{10}$ fatty acid:$C_{12}$ fatty acid at a weight ratio of about 37:7:56, weight-average molecular weight: approximately 570

Tri-CL Oil Fatty Acid Glyceride, Product of NOF Corp.

Glycerin and fatty acid triester with $C_8$ fatty acid:$C_{12}$ fatty acid at a weight ratio of about 44:56, weight-average molecular weight: approximately 570

PANACET 810s, product of NOF Corp.

Glycerin and fatty acid triester with $C_8$ fatty acid:$C_{10}$ fatty acid at a mass ratio of about 85:15, weight-average molecular weight: approximately 480

PANACET 800, Product of NOF Corp.

Glycerin and fatty acid triester with octanoic acid ($C_8$) as the entire fatty acid portion, weight-average molecular weight: approximately 470

PANACET 800B, Product of NOF Corp.

Glycerin and fatty acid triester with 2-ethylhexanoic acid ($C_8$) as the entire fatty acid portion, weight-average molecular weight: approximately 470

NA36, Product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut Fatty Acid Glyceride, Product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic Acid Diglyceride, Product of NOF Corp.
Glycerin and fatty acid diester with octanoic acid as the fatty acid, weight-average molecular weight: approximately 340

[($a_3$) Ester of a Chain Hydrocarbon Diol and at Least One Fatty Acid]

UNISTAR H-208BRS, Product of NOF Corp.
Neopentyl glycol di(2-ethylhexanoate), weight-average molecular weight: approximately 360

COMPOL BL, Product of NOF Corp.
Dodecanoic acid ($C_{12}$) monoester of butylene glycol, weight-average molecular weight: approximately 270

COMPOL BS, Product of NOF Corp.
Octadecanoic acid ($C_{18}$) monoester of butylene glycol, weight-average molecular weight: approximately 350

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, Product of Tokyo Kasei Kogyo Co., Ltd.
Weight-average molecular weight: approximately 400
Tributyl Citrate, Product of Tokyo Kasei Kogyo Co., Ltd.
Weight-average molecular weight: approximately 360

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl Adipate, Product of Wako Pure Chemical Industries, Ltd.
Weight-average molecular weight: approximately 380

[($d_3$) Ester of a Fatty Acid and an Aliphatic Monohydric Alcohol]

ELECTOL WE20, Product of NOF Corp.
Ester of dodecanoic acid ($C_{12}$) and dodecyl alcohol ($C_{12}$), weight-average molecular weight: approximately 360
ELECTOL WE40, Product of NOF Corp.
Ester of tetradecanoic acid ($C_{14}$) and dodecyl alcohol ($C_{12}$), weight-average molecular weight: approximately 390

[($e_1$) Polyoxy $C_3$-$C_6$ Alkylene Glycol]

UNIOL PB500, Product of NOF Corp.
Polybutylene glycol, weight-average molecular weight: approximately 500
UNIOL PB700, Product of NOF Corp.
Polyoxybutylene polyoxypropylene glycol, weight-average molecular weight: approximately 700

[($f_1$) Chain Alkane]

PARLEAM 6, Product of NOF Corp.
Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, Product of NOF Corp.
Glycerin and fatty acid triester obtained by addition of hydrogen to NA36 for reduced proportion of double bonds from unsaturated fatty acid starting material, weight-average molecular weight: approximately 880

(Caprylic Acid/Capric Acid) Monoglyceride, Product of NOF Corp.
Glycerin and fatty acid monoester, with octanoic acid ($C_8$) and decanoic acid ($C_{10}$) at a mass ratio of about 85:15, weight-average molecular weight: approximately 220
Monomuls 90-L2 Lauric Acid Monoglyceride, Product of Cognis Japan
Isopropyl Citrate, Product of Tokyo Kasei Kogyo Co., Ltd.
Weight-average molecular weight: approximately 230
Diisostearyl Malate
Weight-average molecular weight: approximately 640
UNIOL PB1000R, Product of NOF Corp.
Polybutylene glycol, weight-average molecular weight: approximately 1,000
UNIOL D-250, Product of NOF Corp.
Polypropylene glycol, weight-average molecular weight: approximately 250
UNIOL D-400, Product of NOF Corp.
Polypropylene glycol, weight-average molecular weight: approximately 400
UNIOL D-700, Product of NOF Corp.
Polypropylene glycol, weight-average molecular weight: approximately 700
UNIOL D-1000, Product of NOF Corp.
Polypropylene glycol, weight-average molecular weight: approximately 1,000
UNIOL D-1200, Product of NOF Corp.
Polypropylene glycol, weight-average molecular weight: approximately 1,160
UNIOL D-2000, Product of NOF Corp.
Polypropylene glycol, weight-average molecular weight: approximately 2,030
UNIOL D-3000, Product of NOF Corp.
Polypropylene glycol, weight-average molecular weight: approximately 3,000
UNIOL D-4000, Product of NOF Corp.
Polypropylene glycol, weight-average molecular weight: approximately 4,000
PEG1500, Product of NOF Corp.
Polyethylene glycol, weight-average molecular weight: approximately 1,500-1,600
WILBRITE cp9, Product of NOF Corp.
Polybutylene glycol compound with OH groups at both ends esterified by hexadecanoic acid ($C_{16}$), weight-average molecular weight: approximately 1,150
UNILUBE MS-70K, Product of NOF Corp.
Stearyl ether of polypropylene glycol, approximately 15 repeating units, weight-average molecular weight: approximately 1,140
NONION S-6, Product of NOF Corp.
Polyoxyethylene monostearate, approximately 7 repeating units, weight-average molecular weight: approximately 880
UNILUBE 5TP-300 KB
Polyoxyethylene polyoxypropylene pentaerythritol ether, produced by addition of 5 mol of ethylene oxide and 65 mol of propylene oxide to 1 mol of pentaerythritol, weight-average molecular weight: 4,130
WILBRITE s753, Product of NOF Corp.
Polyoxyethylene polyoxypropylene polyoxybutylene glycerin, weight-average molecular weight: approximately 960
UNIOL TG-330, Product of NOF Corp.
Glyceryl ether of polypropylene glycol, approximately 6 repeating units, weight-average molecular weight: approximately 330

UNIOL TG-1000, Product of NOF Corp.

Glyceryl ether of polypropylene glycol, approximately 16 repeating units, weight-average molecular weight: approximately 1,000

UNIOL TG-3000, Product of NOF Corp.

Glyceryl ether of polypropylene glycol, approximately 16 repeating units, weight-average molecular weight: approximately 3,000

UNIOL TG-4000, Product of NOF Corp.

Glyceryl ether of polypropylene glycol, approximately 16 repeating units, weight-average molecular weight: approximately 4,000

UNILUBE DGP-700, Product of NOF Corp.

Diglyceryl ether of polypropylene glycol, approximately 9 repeating units, weight-average molecular weight: approximately 700

UNIOX HC60, Product of NOF Corp.

Polyoxyethylene hydrogenated castor oil, weight-average molecular weight: approximately 3,570

Vaseline, Product of Cognis Japan

Petroleum-Derived Hydrocarbon, Semi-Solid

The kinematic viscosities, water holding percentages, weight-average molecular weights, IOBs and melting points of the samples are shown in Table 2.

For the melting point, "<45" indicates a melting point of below 45° C.

Almost the entire skin contact surface of the top sheet of the sanitary napkin was coated with the aforementioned blood slipping agent. Each blood slipping agent was used directly, when the blood slipping agent was liquid at room temperature, or when the blood slipping agent was solid at room temperature it was heated to a temperature of its melting point+20° C., and then a control seam HMA gun was used for atomization of each blood slipping agent and coating onto the skin contact surface of the top sheet to a basis weight of about 5 g/m².

Figure 8:
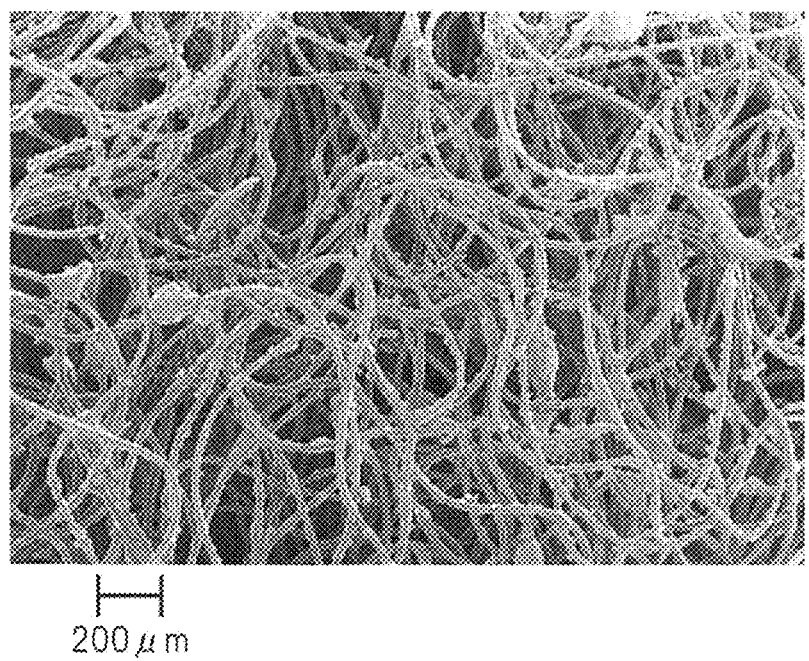
FIG. 8 is an electron micrograph of the skin contact surface of a top sheet in a sanitary napkin wherein the top sheet comprises tri-C2L oil fatty acid glycerides.

FIG. 8 is an electron micrograph of the skin contact surface of a top sheet in a sanitary napkin (No. 1-5) wherein the top sheet comprises tri-C2L oil fatty acid glycerides. As clearly seen in FIG. 8, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood slipping agent, and 3.0 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3.0 g of horse EDTA blood at 37±1° C. was again added dropwise through the acrylic board hole with a pipette (twice).

After the second dropping of blood, the acrylic board was immediately removed and 10 sheets of filter paper (Qualitative filter paper No. 2, product of Advantech Toyo, Inc., 50 mm×35 mm) (total weight of 10 filter sheets: $FW_0$ (g)) were placed on the location where the blood had been dropped, and then a weight was placed thereover at a pressure of 30 g/cm². After 1 minute, the filter paper was removed, the total weight $FW_1$ (g) of the 10 tested filter sheets was measured, and the "rewetting rate" was calculated by the following formula.

$$\text{Rewetting rate (mass \%)} = 100 \times [FW_1(g) - FW_0(g)]/6.0 \text{ (g)}$$

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet (TS) after the absorbent body migration rate test was visually evaluated on the following scale.

VG (Very Good): Virtually no redness of blood remaining, and no clear delineation between areas with and without blood.

G (Good): Slight redness of blood remaining, but difficult to discriminate between areas with and without blood.

F (Fair): Slight redness of blood remaining, areas with blood discernible.

P (Poor): Redness of blood completely remaining.

The tack on the skin contact surface of the top sheet was also measured at 35° C., and evaluated on the following scale.

G: No tack
F: Slight tack
P: Tack

The results are summarized in Table 2 below.

TABLE 2

| No. | Blood slipping agent | Kinematic viscosity (mm²/s, 40° C.) | Water holding percentage (mass %) | Wt.-average mol. wt. | IOB | Melting point (° C.) | Rewetting rate (%) | Absorbent body migration rate (sec) | TS whiteness | Tack |
|---|---|---|---|---|---|---|---|---|---|---|
| 1-1 | H-408BRS | 45 | 0.7 | 640 | 0.13 | <-5 | 1.2 | 3 | VG | G |
| 1-2 | H-2408BRS-22 | 22 | 0.8 | 520 | 0.18 | <-5 | 2.0 | 3 | VG | G |
| 1-3 | Cetiol SB45DEO | | | | 0.16 | 44 | 7.0 | 6 | VG | |
| 1-4 | SOY42 | | | 880 | 0.16 | 43 | 5.8 | 8 | VG | G |
| 1-5 | Tri-C2L oil fatty acid glyceride | 20 | <1.0 | 570 | 0.27 | 37 | 0.3 | 3 | VG | G |
| 1-6 | Tri-CL oil fatty acid glyceride | 15 | <1.0 | 570 | 0.28 | 38 | 1.7 | 3 | VG | G |
| 1-7 | PANACET 810s | 9 | 0.3 | 480 | 0.32 | -5 | 2.8 | 3 | VG | G |
| 1-8 | PANACET 800 | 15 | 0.5 | 470 | 0.33 | -5 | 0.3 | 3 | VG | G |
| 1-9 | PANACET 800B | 20 | <1.0 | 470 | 0.33 | -5 | 2.0 | 3 | VG | G |
| 1-10 | NA36 | 40 | <1.0 | 880 | 0.16 | 37 | 3.9 | 5 | VG | G |
| 1-11 | Tri-coconut oil fatty acid glyceride | 25 | <1.0 | 670 | 0.28 | 30 | 4.3 | 5 | VG | G |
| 1-12 | Caprylic acid diglyceride | 25 | 2.7 | 340 | 0.58 | <45 | 4.2 | 9 | G | G |
| 1-13 | UNISTAR H-208BRS | 8 | 0.7 | 360 | 0.24 | <-5 | 2.0 | 5 | VG | G |
| 1-14 | COMPOL BL | 10 | 1.6 | 270 | 0.50 | 2 | 2.0 | 5 | G | G |

TABLE 2-continued

| No. | Blood slipping agent | Kinematic viscosity (mm²/s, 40° C.) | Water holding percentage (mass %) | Wt.-average mol. wt. | IOB | Melting point (° C.) | Rewetting rate (%) | Absorbent body migration rate (sec) | TS whiteness | Tack |
|---|---|---|---|---|---|---|---|---|---|---|
| 1-15 | COMPOL BS | 35 | 0.3 | 350 | 0.36 | 37 | 7.9 | 9 | G | G |
| 1-16 | Tributyl O-acetylcitrate | 15 | 0.9 | 400 | 0.60 | <45 | 6.2 | 8 | VG | G |
| 1-17 | Tributyl citrate | 12 | 0.6 | 360 | 0.78 | <45 | 3.0 | 6 | G | G |
| 1-18 | Dioctyl adipate | 7 | 0.4 | 380 | 0.27 | <45 | 1.7 | 6 | VG | G |
| 1-19 | ELECTOL WE20 | 10 | 0.3 | 360 | 0.13 | 29 | 1.8 | 5 | VG | G |
| 1-20 | ELECTOL WE40 | 15 | 0.5 | 390 | 0.12 | 37 | 1.8 | 4 | VG | G |
| 1-21 | UNIOL PB500 | 40 | 3.6 | 500 | 0.44 | <45 | 4.5 | 4 | G | G |
| 1-22 | UNIOL PB700 | 50 | 2.3 | 700 | 0.49 | −5 | 2.8 | 5 | G | G |
| 1-23 | PARLEAM 6 | 5 | 0.06 | 330 | 0.00 | −5 | 6.0 | 8 | VG | G |
| 1-24 | NA50 | 80<< | —* | 880 | 0.18 | 52 | 15.5 | 60 | P | G |
| 1-25 | (Caprylic acid/Capric acid) monoglyceride | 70 | 4.0<< | 220 | 1.15 | <45 | 4.0 | 4 | P | G |
| 1-26 | 90-L2 Lauric acid monoglyceride | 80<< | 4.0<< | <1,000 | 0.87 | 58 | 6.2 | 7 | P | G |
| 1-27 | Isopropyl citrate | 120 | 4.0<< | 230 | 1.56 | <45 | 12.2 | 5 | G | F |
| 1-28 | Diisostearyl malate | 450 | 4.0<< | 640 | 0.28 | <45 | 5.5 | 8 | F | F |
| 1-29 | UNIOL PB1000R | 70 | 5.5 | 1000 | 0.40 | <45 | 4.0 | 4 | G | F |
| 1-30 | UNIOL D-250 | 20 | 4.0<< | 250 | | <45 | — | — | P | G |
| 1-31 | UNIOL D-400 | 30 | 4.0<< | 400 | 0.76 | <45 | 8.7 | 40 | P | G |
| 1-32 | UNIOL D-700 | 50 | 34.6 | 700 | 0.58 | <45 | 7.5 | — | F | G |
| 1-33 | UNIOL D-1000 | 70 | 26.7 | 1,000 | 0.51 | <45 | 6.8 | 15 | F | F |
| 1-34 | UNIOL D-1200 | 90 | 16.2 | 1,160 | 0.48 | <45 | 0.5 | 11 | F | F |
| 1-35 | UNIOL D-2000 | 160 | | 2,030 | | <45 | — | — | F | P |
| 1-36 | UNIOL D-3000 | | 0.6 | 3,000 | 0.39 | <45 | 1.7 | 10 | F | P |
| 1-37 | UNIOL D-4000 | 450 | 0.5 | 4,000 | 0.38 | <45 | 1.0 | 7 | G | P |
| 1-38 | PEG1500 | 120 | 4.0<< | 1,500-1,600 | 0.78 | 40 | 11.0 | 38 | P | P |
| 1-39 | WILBRITE CP9 | 120 | 0.6 | 1,150 | 0.21 | 35 | 1.4 | 3 | G | P |
| 1-40 | UNILUBE MS-70K | 50 | 2.8 | 1,140 | 0.30 | <−10 | 6.7 | 3 | G | F |
| 1-41 | NONION S-6 | 65 | 4.0<< | 880 | 0.44 | 37 | 8.4 | 7 | P | G |
| 1-42 | UNILUBE 5TP-300KB | 310 | 3.9 | 4,130 | 0.39 | <45 | 2.0 | 6 | G | P |
| 1-43 | WILBRITE s753 | 120 | 27.3 | 960 | 0.67 | −5 | 9.3 | 9 | F | F |
| 1-44 | UNIOL TG-330 | 30 | | 330 | 1.27 | <45 | — | — | — | G |
| 1-45 | UNIOL TG-1000 | 100 | 21.2 | 1,000 | 0.61 | <45 | 14.2 | 7 | G | G |
| 1-46 | UNIOL TG-3000 | 230 | 4.3 | 3,000 | 0.42 | <45 | 0.8 | 6 | G | P |
| 1-47 | UNIOL TG-4000 | 300 | 2.4 | 4,000 | 0.40 | <45 | 2.0 | 6 | G | P |
| 1-48 | UNILUBE DGP-700 | 200 | 4.0<< | 700 | 0.91 | <0 | 8.0 | 10 | F | F |
| 1-49 | UNIOX HC60 | 1150 | | 3,570 | 0.46 | 33 | 14.6 | 46 | P | P |
| 1-50 | Vaseline | 80<< | 0.0 | <1,000 | 0.00 | 55 | 9.7 | 10 | F | P |
| 1-51 | None | — | — | — | — | — | 22.7 | 60< | P | G |

*High viscosity, umeasureable.

In the absence of a blood slipping agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance.

This suggests that, since the blood slipping agent has a high absorbent body migration rate, the blood slipping agent-containing region in the ridges of the nonwoven fabric of this disclosure causes menstrual blood that has reached the ridges to rapidly slip into the absorbent body before being diffused in the longwise direction.

Similarly, it was found that the absorption performance is greatly improved with a blood slipping agent having a kinematic viscosity of about 0.01 to 80 mm²/s at 40° C., a water holding percentage of about 0.01 to about 4.0 mass %, and a weight-average molecular weight of less than about 1,000.

Next, several volunteer participants were asked to wear sanitary napkins Nos. 1-1 to 1-51, and the obtained responses indicated that with the sanitary napkins comprising blood slipping agent Nos. 1-1 to 1-23, the top sheets had no sticky feel and the top sheets were smooth, even after absorption of menstrual blood.

Also, with sanitary napkins that comprised blood slipping agent Nos. 1-11, 1-13, 1-16, 1-18 to 1-20 and 1-23, the skin contact surfaces of the top sheets after absorption of menstrual blood was not reddened by the blood and the unpleasantness was minimal.

Example 2

[Surface Residue Rate of Menstrual Blood on Top Sheet with Ridge-Furrow Structure]

The surface residue rate of menstrual blood on a top sheet with a ridge-furrow structure was evaluated.

There were prepared a top sheet, formed of a hydrophilic agent-treated air-through nonwoven fabric (composite fiber composed of polyester and polyethylene terephthalate, basis weight: 35 g/m²), a second sheet, formed of an air-through nonwoven fabric (composite fiber composed of polyester and polyethylene terephthalate, basis weight: 30 g/m²), an absorbent body comprising pulp (basis weight: 150 to 450 g/m², increased at the center section), an acrylic superabsorbent polymer (basis weight: 15 g/m²) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, the pitch of the ridge-furrow structure (ridge width+furrow width) was approximately 4 mm, and through-holes (openings) were formed in the furrows at an open area ratio of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1.

Sanitary napkins No. 2-2 to No. 2-40 were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m².

The blood slipping agent was coated onto essentially the entire skin contact surface of the top sheet, and on both the ridges and furrows.

[Test Methods]

After measuring the weight: $W_2$ (g) of the top sheet (the weight of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of the top sheet after the test) was measured and the "surface residue rate A (mass %)" was calculated by the following formula.

Surface residue rate (mass %)=100×[$W_3$(g)−$W_2$(g)]/ 4.0(g)

The results are shown in Table 3 below.

TABLE 3

| No. | Blood slipping agent | Surface residue rate (mass %) |
|---|---|---|
| 2-1 | H-408BRS | 0.8 |
| 2-2 | H-2408BRS-22 | 0.8 |
| 2-3 | PANACET 810s | 0.8 |
| 2-4 | PANACET 800 | 1.8 |
| 2-5 | Caprylic acid diglyceride | 1.0 |
| 2-6 | UNISTAR H-208BRS | 0.5 |
| 2-7 | COMPOL BL | 1.3 |
| 2-8 | COMPOL BS | 2.5 |
| 2-9 | Tributyl O-acetylcitrate | 0.5 |
| 2-10 | Tributyl citrate | 1.8 |
| 2-11 | Dioctyl adipate | 1.5 |
| 2-12 | ELECTOL WE20 | 0.5 |
| 2-13 | ELECTOL WE40 | 2.3 |
| 2-14 | UNIOL PB500 | 2.5 |
| 2-15 | UNIOL PB700 | 1.3 |
| 2-16 | PARLEAM 6 | 2.0 |

TABLE 3-continued

| No. | Blood slipping agent | Surface residue rate (mass %) |
|---|---|---|
| 2-17 | NA50 | 4.3 |
| 2-18 | (Caprylic acid/capric acid) monoglyceride | 5.0 |
| 2-19 | 90-L2 Lauric acid monoglyceride | 5.0 |
| 2-20 | Isopropyl citrate | 4.8 |
| 2-21 | Diisostearyl malate | 3.3 |
| 2-22 | UNIOL PB1000R | 2.5 |
| 2-23 | UNIOL D-250 | 3.8 |
| 2-24 | UNIOL D-400 | 4.8 |
| 2-25 | UNIOL D-700 | 4.8 |
| 2-26 | UNIOL D-1000 | 3.8 |
| 2-27 | UNIOL D-1200 | 3.0 |
| 2-28 | UNIOL D-3000 | 3.0 |
| 2-29 | UNIOL D-4000 | 2.5 |
| 2-30 | PEG1500 | 5.5 |
| 2-31 | WILBRITE CP9 | 6.8 |
| 2-32 | UNILUBE MS-70K | 1.5 |
| 2-33 | UNILUBE 5TP-300KB | 2.0 |
| 2-34 | WILBRITE s753 | 3.5 |
| 2-35 | UNIOL TG-1000 | 3.5 |
| 2-36 | UNIOL TG-3000 | 1.0 |
| 2-37 | UNIOL TG-4000 | 2.0 |
| 2-38 | UNILUBE DGP-700 | 3.5 |
| 2-39 | Vaseline | 4.0 |
| 2-40 | None | 7.5 |

With sanitary napkin No. 2-40, which had no blood slipping agent, the surface residue rate was 7.5 mass %, but with sanitary napkins No. 2-1 to No. 2-16 wherein the kinematic viscosity and water holding percentage were within the prescribed ranges, the surface residue rate was 2.5 mass % or lower.

With sanitary napkins No. 2-1 to No. 2-16, it was observed that the horse EDTA blood that was dropped onto the ridges of the top sheet slipped down from the ridges into the furrows, and was rapidly absorbed from the furrows into the absorbent body. However, with sanitary napkin No. 2-40 which had no blood slipping agent, the dropped horse EDTA blood did not slip down into the furrows but slowly dripped down into the furrows, most of it remaining on the ridges of the top sheet. Also, with the absorbent articles with high water holding percentage, as with No. 2-25, for example, the horse EDTA blood that was dropped onto the ridges of the top sheet did not slip down into the furrows but slowly dripped while partially remaining on the top sheet, and a portion thereof remained on the ridges.

The following experiment was also conducted in order to confirm the function of the blood slipping agent.

Example 3

[Viscosity of Blood Containing Blood Slipping Agent]

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the present disclosure has an effect of lowering the viscosity of blood, such as menstrual blood in the low viscosity range. Lowering the blood viscosity presumably allows absorbed menstrual blood to more easily migrate rapidly from the top sheet to the absorbent body.

Example 4

[Photomicrograph of Blood Slipping Agent-containing Blood]

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 9(a), and a photomicrograph of menstrual blood containing PANACET 810s is shown in FIG. 9(b).

Figure 9:
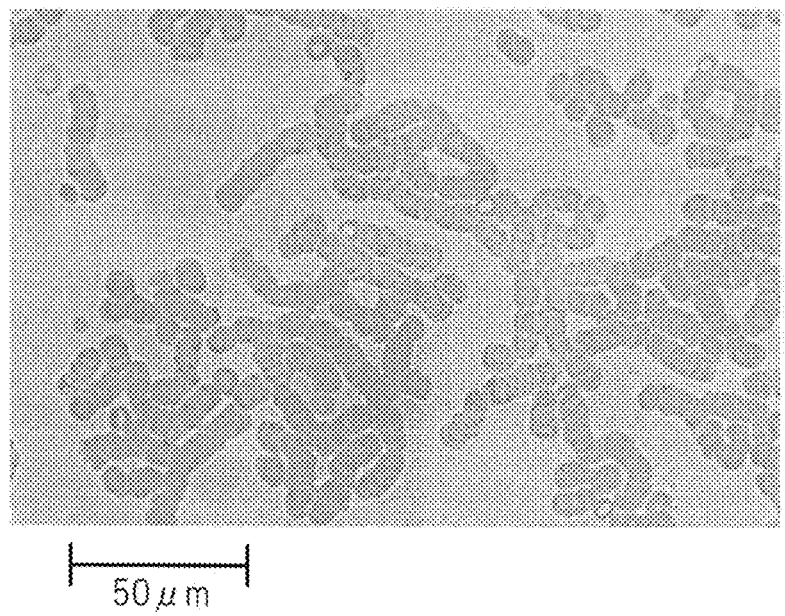
FIG. 9 is a pair of photomicrographs of menstrual blood containing and not containing a blood slipping agent.
Figure 9:
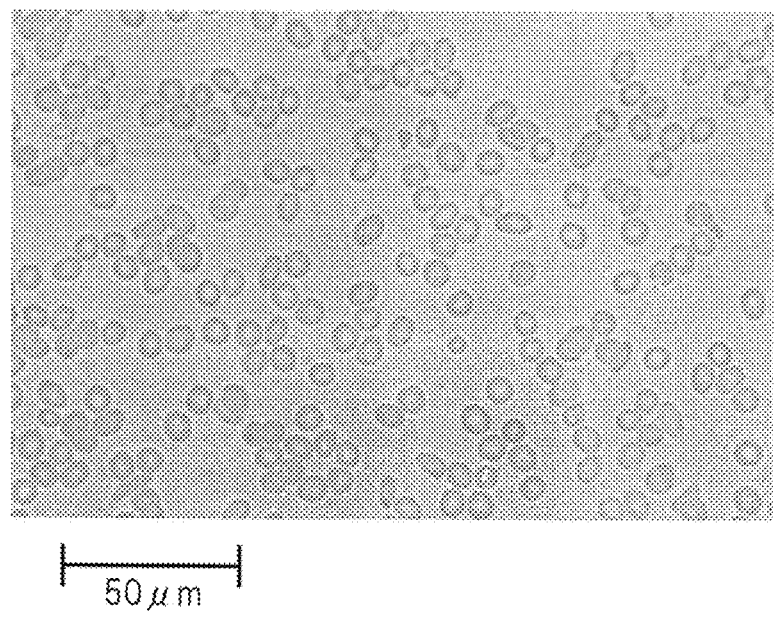

From FIGS. 9(a) and 9(b), it is seen that the erythrocytes formed aggregates, such as rouleaux in the menstrual blood containing no blood slipping agent, while the erythrocytes were stably dispersed in the menstrual blood containing PANACET 810s. This suggests that the blood slipping agent functions to stabilize erythrocytes in blood.

Example 5

[Surface Tension of Blood Containing Blood Slipping Agent]

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 10:
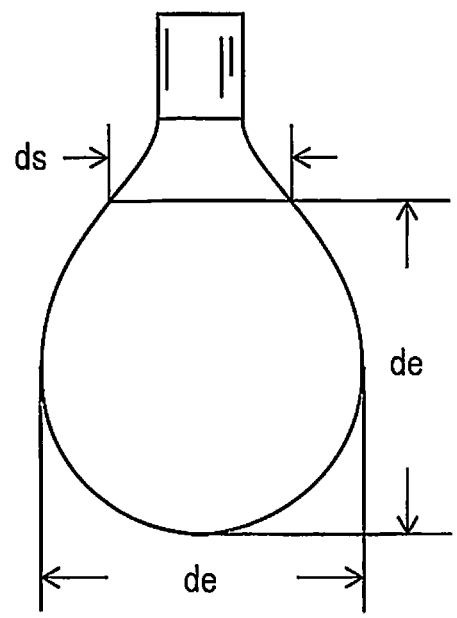
FIG. 10 is a diagram illustrating a method of measuring surface tension.

The measurement was accomplished automatically with a device, and the surface tension y was determined by the following formula (see FIG. 10).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 4 below.

TABLE 4

| No. | Blood slipping agent Type | Amount (mass %) | Measuring temperature (° C.) | Surface tension (mN/m) |
|---|---|---|---|---|
| 5-1 | — | — | 35 | 62.1 |
| 5-2 | PANACET | 0.01 | 35 | 61.5 |
| 5-3 | 810s | 0.05 | 35 | 58.2 |
| 5-4 | | 0.10 | 35 | 51.2 |
| 5-5 | ELECTOL WE20 | 0.10 | 35 | 58.8 |
| 5-6 | PARLEAM 6 | 0.10 | 35 | 57.5 |
| 5-7 | — | — | 50 | 56.3 |
| 5-8 | WILBRITE cp9 | 0.10 | 50 | 49.1 |

Based on Table 4 it is seen that the blood slipping agent has an effect of lowering the surface tension of blood.

Lowering the surface tension of blood presumably allows absorbed blood to rapidly migrate from the top sheet to the absorbent body, without being retained between the top sheet fibers.

The present disclosure relates to the following J1 to J10.

[J1]

A nonwoven fabric for a top sheet of an absorbent article, having a longwise direction and a crosswise direction, the nonwoven fabric having a plurality of ridges and a plurality of furrows extending in the longwise direction and alternately disposed in the crosswise direction, wherein the plurality of ridges and the plurality of furrows each have a plurality of through-holes, each of the ridges has a blood slipping agent-containing region that contains a blood slipping agent with a kinematic viscosity of 0.01 to 80 mm$^2$/s at 40° C., a water holding percentage of 0.01 to 4.0 mass % and a weight-average molecular weight of less than 1,000.

[J2]

The nonwoven fabric according to J1, wherein the blood slipping agent further has an IOB of 0.00 to 0.60.

[J3]

The nonwoven fabric according to J1 or J2, wherein each of the furrows has, as through-holes, a plurality of openings formed by reducing fibers of the nonwoven fabric at the furrows, and the fabric has joints that connect every two adjacent ridges between every two adjacent openings.

[J4]

The nonwoven fabric according to J3, wherein at the joints, a content of fibers oriented in the crosswise direction is higher than a content of fibers oriented in the longwise direction.

[J5]

The nonwoven fabric according to any one of J1 to J4, wherein the through-holes of the ridges include perforated sections formed by perforation.

[J6]

The nonwoven fabric according to any one of J1 to J5, having 0.5 to 5.0 through-holes per 1 cm$^2$ area of the nonwoven fabric.

[J7]

The nonwoven fabric according to any one of J1 to J6, wherein the ridges include a blood slipping agent with a basis weight of 1 to 30 g/m$^2$ in the blood slipping agent-containing regions.

[J8]

The nonwoven fabric according to any one of J1 to J7, wherein the blood slipping agent is selected from the group consisting of following items (i) to (iii), and any combination thereof:

(i) a hydrocarbon;

(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

[J9]

The nonwoven fabric according to any one of J1 to J8, wherein the blood slipping agent is selected from the group consisting of following items (i') to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when two or more same or different bonds are inserted in the compound of (ii') or (iii'), the bonds are not adjacent.

[J10]

The nonwoven fabric according to any one of J1 to J9, wherein the blood slipping agent is selected from the group consisting of following items (A) to (F), as well as any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

[J11]

The nonwoven fabric according to any one of J1 to J10, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

[J12]

The nonwoven fabric according to any one of J1 to J11, wherein the blood slipping agent is adhering to surfaces of fibers of the nonwoven fabric.

[J13]

An absorbent article comprising a liquid-permeable top sheet, a liquid-impermeable back sheet and an absorbent body between the top sheet and back sheet, wherein the top sheet is the nonwoven fabric according to any one of J1 to J12.

[J14]

The absorbent article according to J13, wherein the longwise direction is parallel to the lengthwise direction of the absorbent article.

[J15]

The absorbent article according to any one of J1 to J14, which is a sanitary napkin or panty liner.

REFERENCE SIGNS LIST

1 Nonwoven fabric
2 Ridge
3 Furrow
4 Through-hole
4' Perforated section
4" Opening
5 Joint
11 Absorbent article
12 Top sheet
13 Absorbent body
14 Side flap
15 Side sheet
16 Embossing
17 Blood slipping agent-containing region
18 Back sheet
21 Projection
22 Recess
23 Skin contact surface
24 Blood slipping agent
25, 25', 25" Menstrual blood

The invention claimed is:

1. A nonwoven fabric for a top sheet of an absorbent article, having a longwise direction and a crosswise direction,
the nonwoven fabric having a plurality of ridges and a plurality of furrows extending in the longwise direction and alternately disposed in the crosswise direction,
wherein the plurality of ridges and the plurality of furrows each have a plurality of through-holes,
each of the ridges and at least one through-hole of the plurality of through-holes has a blood slipping agent-containing region having a coating consisting essentially of a blood slipping agent with a kinematic viscosity of 0.01 to 80 mm$^2$/s at 40° C, a water holding percentage of 0.01 to 4.0 mass% and a weight-average molecular weight of less than 1,000,
wherein the water holding percentage of the blood slipping agent causes the blood slipping agent to exhibit an affinity with menstrual blood, and the kinematic viscosity of the blood slipping agent causes the blood slipping agent to migrate through the top sheet with the menstrual blood,
wherein each of the furrows has, as through-holes, a plurality of openings formed by reducing fibers of the nonwoven fabric at the furrows, and the fabric has joints that connect every two adjacent ridges between every two adjacent openings, and each of the two adjacent openings extend across an entirety of a distance between adjacent ridges of the plurality of ridges.

2. The nonwoven fabric according to claim 1, wherein the blood slipping agent further has an Inorganic Organic Balance (IOB) of 0.00 to 0.60.

3. The nonwoven fabric according to claim 1, wherein at the joints, a content of fibers oriented in the crosswise direction is higher than a content of fibers oriented in the longwise direction.

4. The nonwoven fabric according to claim 1, wherein the through-holes of the ridges include perforated sections formed by perforation.

5. The nonwoven fabric according to claim 1, having 0.5 to 5.0 through-holes per 1 cm$^2$ area of the nonwoven fabric.

6. The nonwoven fabric according to claim 1, wherein the blood slipping agent has a basis weight of 1 to 30 g/m$^2$.

7. The nonwoven fabric according to claim 1, wherein the blood slipping agent is selected from the group consisting of following items (i) to (iii), and any combination thereof:
(i) a hydrocarbon;
(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—C—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;
with the proviso that when two or more oxy groups are inserted in the compound of (ii) or (iii), the oxy groups are not adjacent.

8. The nonwoven fabric according to claim 1, wherein the blood slipping agent is selected from the group consisting of following items (i') to (iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;
with the proviso that when two or more same or different bonds are inserted in the compound of (ii') or (iii'), the bonds are not adjacent.

9. The nonwoven fabric according to claim 1, wherein the blood slipping agent is selected from the group consisting of following items (A) to (F), as well as any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;
(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;
(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;
(E) a polyoxy $C_3$-$C_6$ alkylene glycol, or alkyl ester or alkyl ether thereof; and
(F) a chain hydrocarbon.

10. The nonwoven fabric according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

11. The nonwoven fabric according to claim 1, wherein the blood slipping agent is adhering to surfaces of fibers of the nonwoven fabric.

12. An absorbent article comprising a liquid-permeable top sheet, a liquid-impermeable back sheet and an absorbent body between the top sheet and back sheet, wherein
the top sheet is the nonwoven fabric according to claim 1.

13. The absorbent article according to claim 12, wherein the longwise direction is parallel to the lengthwise direction of the absorbent article.

14. The absorbent article according to claim 1, which is a sanitary napkin or panty liner.

15. An absorbent article comprising:
a liquid-permeable top sheet;
a liquid-impermeable back sheet; and
an absorbent body between the top sheet and back sheet, wherein
the top sheet is the nonwoven fabric comprises a nonwoven fabric having a longwise direction and a crosswise direction,
the nonwoven fabric having a plurality of ridges and a plurality of furrows extending in the longwise direction and alternately disposed in the crosswise direction,
wherein each ridge of the plurality of ridges and each furrow of the plurality of furrows has a plurality of through-holes,
a blood slipping agent-containing composition on each ridge of the plurality of ridges, at least one through-hole of the plurality of through-holes, and on each joint of the plurality of joints, wherein the blood slipping agent-containing composition consists essentially of a blood slipping agent having a kinematic viscosity of 0.01 to 80 mm$^2$/s at 40° C., a water holding percentage of 0.01 to 4.0 mass% and a weight-average molecular weight of less than 1,000, and
wherein the water holding percentage of the blood slipping agent causes the blood slipping agent-containing composition to exhibit an affinity with menstrual blood, and the kinematic viscosity of the blood slipping agent causes the blood slipping agent-containing composition to drop from the top sheet into the absorbent body along with the menstrual blood,
wherein each of the furrows has, as through-holes, a plurality of openings formed by reducing fibers of the nonwoven fabric at the furrows, and the fabric has joints that connect every two adjacent ridges between every two adjacent openings, and each of the two adjacent openings extend across an entirety of a distance between adjacent ridges of the plurality of ridges.

16. A nonwoven fabric for a top sheet of an absorbent article, having a longwise direction and a crosswise direction,
the nonwoven fabric having a plurality of ridges and a plurality of furrows extending in the longwise direction and alternately disposed in the crosswise direction,
wherein the plurality of ridges and the plurality of furrows each have a plurality of through-holes,
each of the ridges has a blood slipping agent-containing region having a coating consisting of a blood slipping agent with a kinematic viscosity of 0.01 to 80 mm$^2$/s at 40° C., a water holding percentage of 0.01 to 4.0 mass% and a weight-average molecular weight of less than 1,000.

17. The absorbent article according to claim 1, wherein each ridge of the plurality of ridges extends across an entirety of an excretory opening contact region of the top sheet.

18. The absorbent article according to claim 1, wherein each joint of the joints comprises a joint through-hole separated from the two adjacent openings.

* * * * *